US011896496B2

(12) United States Patent
Ashleigh et al.

(10) Patent No.: US 11,896,496 B2
(45) Date of Patent: *Feb. 13, 2024

(54) DEVICE AND METHOD FOR DEPLOYMENT OF AN ANCHORING DEVICE FOR INTERVERTEBRAL SPINAL FUSION

(71) Applicant: GLOBUS MEDICAL, INC., Audubon, PA (US)

(72) Inventors: Michael Ashleigh, Phoenixville, PA (US); Noah Hansell, King of Prussia, PA (US); Anand Balasubramanian, Collegeville, PA (US); Kurt Faulhaber, Renton, WA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/656,238

(22) Filed: Mar. 24, 2022

(65) Prior Publication Data

US 2022/0211518 A1 Jul. 7, 2022

Related U.S. Application Data

(60) Continuation of application No. 16/458,909, filed on Jul. 1, 2019, now Pat. No. 11,311,387, which is a
(Continued)

(51) Int. Cl.
*A61F 2/44* (2006.01)
*A61F 2/46* (2006.01)
*A61F 2/30* (2006.01)

(52) U.S. Cl.
CPC ............ *A61F 2/4455* (2013.01); *A61F 2/447* (2013.01); *A61F 2/4611* (2013.01); *A61F 2/4603* (2013.01); *A61F 2002/304* (2013.01); *A61F 2002/30197* (2013.01); *A61F 2002/30383* (2013.01); *A61F 2002/30405* (2013.01); *A61F 2002/30525* (2013.01); *A61F 2002/30556* (2013.01); *A61F 2002/30571* (2013.01); *A61F 2002/30579* (2013.01); *A61F 2002/30593* (2013.01);
(Continued)

(58) Field of Classification Search
CPC ....... A61F 2/4455; A61F 2/447; A61F 2/4611
See application file for complete search history.

(56) References Cited

U.S. PATENT DOCUMENTS 4,349,921 A 9/1982 Kuntz
4,599,086 A 7/1986 Doty
(Continued)

FOREIGN PATENT DOCUMENTS

CA 2088066 A1 1/1992
CH 708531 A2 3/2015
(Continued)

*Primary Examiner* — Si Ming Ku

(57) ABSTRACT

A device and methods for intervertebral spinal fusion of adjacent intervertebral bodies. An intervertebral spacer is positioned within a narrow disc space between adjacent intervertebral bodies of a patient. The spacer is arranged with upper and lower guides. The guides are adapted to simultaneously guide the deployment of upper and lower anchors of an anchoring device into their respective intervertebral bodies. The spacer is also adapted to lock the upper and lower anchors to the spacer in the deployed position.

8 Claims, 27 Drawing Sheets

Related U.S. Application Data division of application No. 14/718,514, filed on May 21, 2015, now Pat. No. 10,376,378.

(52) U.S. Cl.
CPC ............... *A61F 2002/30828* (2013.01); *A61F 2002/30836* (2013.01); *A61F 2002/30845* (2013.01); *A61F 2002/30904* (2013.01); *A61F 2002/4627* (2013.01); *A61F 2220/0008* (2013.01); *A61F 2230/0073* (2013.01)

(56) References Cited

U.S. PATENT DOCUMENTS

| | | | |
|---|---|---|---|
| 4,863,476 A | 9/1989 | Shepperd | |
| 4,863,477 A | 9/1989 | Monson | |
| 5,123,926 A | 6/1992 | Pisharodi | |
| 5,290,312 A | 3/1994 | Kojimoto et al. | |
| 5,306,310 A | 4/1994 | Siebels | |
| 5,375,823 A | 12/1994 | Navas | |
| 5,390,683 A | 2/1995 | Pisharodi | |
| 5,522,899 A | 6/1996 | Michelson | |
| 5,534,030 A | 7/1996 | Navarro et al. | |
| 5,554,191 A | 9/1996 | Lahille et al. | |
| 5,571,192 A | 11/1996 | Schonhoffer | |
| 5,645,596 A | 7/1997 | Kim | |
| 5,653,763 A | 8/1997 | Errico et al. | |
| 5,665,122 A | 9/1997 | Kambin | |
| 5,676,701 A | 10/1997 | Yuan et al. | |
| 5,849,004 A | 12/1998 | Bramlet | |
| 6,039,761 A | 3/2000 | Li et al. | |
| 6,045,579 A | 4/2000 | Hochschuler et al. | |
| 6,080,193 A | 6/2000 | Hochschuler et al. | |
| 6,099,531 A | 8/2000 | Bonutti | |
| 6,126,689 A | 10/2000 | Brett | |
| 6,176,882 B1 | 1/2001 | Biedermann et al. | |
| 6,258,125 B1 | 7/2001 | Paul et al. | |
| 6,447,546 B1 | 9/2002 | Bramlet et al. | |
| 6,558,423 B1 | 5/2003 | Michelson | |
| 6,562,074 B2 | 5/2003 | Gerbec et al. | |
| 6,576,016 B1 | 6/2003 | Hochschuler et al. | |
| 6,554,863 B2 | 8/2003 | Paul et al. | |
| 6,641,614 B1 | 11/2003 | Wagner et al. | |
| 6,648,917 B2 | 11/2003 | Gerbec et al. | |
| 6,666,891 B2 | 12/2003 | Boehm, Jr. et al. | |
| 6,692,495 B1 | 2/2004 | Zacouto | |
| 6,706,070 B1 | 3/2004 | Wagner et al. | |
| 6,752,832 B2 | 6/2004 | Ulrich | |
| 6,814,756 B1 | 11/2004 | Michelson | |
| 6,830,589 B2 | 12/2004 | Erickson | |
| 6,849,093 B2 | 2/2005 | Michelson | |
| 6,852,129 B2 | 2/2005 | Gerbec et al. | |
| 6,863,673 B2 | 3/2005 | Gerbec et al. | |
| 6,881,228 B2 | 4/2005 | Zdeblick et al. | |
| 7,018,415 B1 | 3/2006 | McKay | |
| 7,070,598 B2 | 7/2006 | Lim et al. | |
| 7,204,853 B2 | 4/2007 | Gordon | |
| 7,217,291 B2 | 5/2007 | Zucherman et al. | |
| 7,282,063 B2 | 10/2007 | Cohen et al. | |
| 7,316,714 B2 | 1/2008 | Gordon | |
| 7,473,276 B2 | 1/2009 | Aebi et al. | |
| 7,547,325 B2 | 6/2009 | Biedermann et al. | |
| 7,621,953 B2 | 11/2009 | Braddock, Jr. et al. | |
| 7,641,693 B2 | 1/2010 | Gutlin et al. | |
| 7,682,396 B2 | 3/2010 | Beaurain et al. | |
| 7,695,516 B2 | 4/2010 | Zeegers | |
| 7,749,270 B2 | 7/2010 | Peterman | |
| 7,753,958 B2 | 7/2010 | Gordon | |
| 7,771,473 B2 | 8/2010 | Thramann | |
| 7,780,732 B2 | 8/2010 | Abernathie | |
| 7,799,081 B2 | 9/2010 | McKinley | |
| 7,815,683 B2 | 10/2010 | Melkent et al. | |
| 7,837,734 B2 | 11/2010 | Zucherman et al. | |
| 7,875,078 B2 | 1/2011 | Wysocki et al. | |
| 7,901,409 B2 | 3/2011 | Canaveral et al. | |
| 7,909,869 B2 | 3/2011 | Gordon | |
| 7,951,199 B2 | 5/2011 | Miller | |
| 7,985,256 B2 | 7/2011 | Grotz et al. | |
| 8,062,375 B2 | 11/2011 | Glerum | |
| 8,070,813 B2 | 12/2011 | Grotz et al. | |
| 8,123,810 B2 | 2/2012 | Gordon | |
| 8,137,405 B2 | 3/2012 | Kostuik et al. | |
| 8,192,495 B2 | 6/2012 | Simpson et al. | |
| 8,303,663 B2 | 11/2012 | Jimenez et al. | |
| 8,343,219 B2 | 1/2013 | Allain et al. | |
| 8,377,140 B2 | 2/2013 | DeFalco et al. | |
| 8,394,129 B2 | 3/2013 | Lopez et al. | |
| 8,394,143 B2 | 3/2013 | Grotz et al. | |
| 8,435,296 B2 | 5/2013 | Kadaba et al. | |
| 8,454,695 B2 | 6/2013 | Grotz et al. | |
| 8,460,388 B2 | 6/2013 | Kirwan et al. | |
| 8,617,245 B2 | 12/2013 | Brett | |
| 8,641,766 B2 | 2/2014 | Donner et al. | |
| 8,647,386 B2 | 2/2014 | Gordon | |
| 8,685,104 B2 | 4/2014 | Lee et al. | |
| 8,696,751 B2 | 4/2014 | Ashley et al. | |
| 8,771,360 B2 | 7/2014 | Jimenez et al. | |
| 8,894,710 B2 | 11/2014 | Simpson et al. | |
| 8,932,355 B2 | 1/2015 | Grotz et al. | |
| 8,940,049 B1 | 1/2015 | JImenez et al. | |
| 8,956,413 B2 | 2/2015 | Ashley et al. | |
| 8,968,405 B2 | 3/2015 | Kirwan et al. | |
| 8,992,620 B2 | 3/2015 | Ashley et al. | |
| 9,028,550 B2 | 5/2015 | Shulock et al. | |
| 9,039,774 B2 | 5/2015 | Chataigner et al. | |
| 9,044,337 B2 | 6/2015 | Dinville et al. | |
| 9,161,842 B2 | 10/2015 | Chin et al. | |
| 9,173,745 B2 | 11/2015 | Dinville et al. | |
| 9,358,125 B2 | 6/2016 | JImenez et al. | |
| 9,532,883 B2 | 1/2017 | McLuen et al. | |
| 9,622,878 B2 | 4/2017 | Grotz | |
| 2002/0045945 A1 | 4/2002 | Liu | |
| 2002/0068976 A1 | 6/2002 | Jackson | |
| 2002/0068977 A1 | 6/2002 | Jackson | |
| 2003/0176926 A1 | 9/2003 | Boehm et al. | |
| 2003/0187436 A1 | 10/2003 | Bolger et al. | |
| 2004/0030387 A1 | 2/2004 | Landry et al. | |
| 2004/0049271 A1 | 3/2004 | Biedermann | |
| 2004/0054412 A1 | 3/2004 | Gerbec et al. | |
| 2004/0087947 A1 | 5/2004 | Lim et al. | |
| 2004/0153065 A1 | 8/2004 | Lim | |
| 2005/0021041 A1 | 1/2005 | Michelson | |
| 2005/0021145 A1 | 1/2005 | de Villiers et al. | |
| 2005/0033432 A1 | 2/2005 | Gordon | |
| 2005/0049590 A1 | 3/2005 | Alleyne et al. | |
| 2005/0080422 A1 | 4/2005 | Otte et al. | |
| 2005/0113916 A1 | 5/2005 | Branch | |
| 2005/0149188 A1 | 7/2005 | Cook | |
| 2005/0171541 A1 | 8/2005 | Boehm | |
| 2005/0251258 A1 | 11/2005 | Jackson | |
| 2005/0273171 A1 | 12/2005 | Gordon | |
| 2005/0273174 A1 | 12/2005 | Gordon | |
| 2005/0278026 A1 | 12/2005 | Gordon | |
| 2005/0283244 A1 | 12/2005 | Gordon | |
| 2005/0283245 A1 | 12/2005 | Gordon | |
| 2006/0004453 A1 | 1/2006 | Bartish et al. | |
| 2006/0015184 A1 | 1/2006 | Winterbottom et al. | |
| 2006/0058878 A1 | 3/2006 | Michelson | |
| 2006/0084986 A1 | 4/2006 | Grinberg et al. | |
| 2006/0122701 A1 | 6/2006 | Kister | |
| 2006/0129244 A1 | 6/2006 | Ensign | |
| 2006/0142859 A1 | 6/2006 | Mcluen | |
| 2006/0149385 A1 | 7/2006 | Mckay | |
| 2006/0195192 A1 | 8/2006 | Gordon et al. | |
| 2006/0229729 A1 | 10/2006 | Gordon | |
| 2006/0241770 A1 | 10/2006 | Rhoda et al. | |
| 2006/0253201 A1 | 11/2006 | Mcluen | |
| 2007/0043442 A1 | 2/2007 | Abernathie | |
| 2007/0050030 A1 | 3/2007 | Kim | |
| 2007/0050032 A1 | 3/2007 | Gittings et al. | |
| 2007/0055377 A1 | 3/2007 | Hanson et al. | |
| 2007/0191951 A1 | 8/2007 | Branch | |
| 2007/0255415 A1 | 11/2007 | Edie et al. | |
| 2007/0270960 A1 | 11/2007 | Bonin, Jr. et al. | |

(56) References Cited

U.S. PATENT DOCUMENTS

| | | |
|---|---|---|
| 2007/0270963 A1 | 11/2007 | Melkent et al. |
| 2007/0270968 A1 | 11/2007 | Baynham |
| 2008/0021559 A1 | 1/2008 | Thramann |
| 2008/0065222 A1 | 3/2008 | Hamada |
| 2008/0114467 A1 | 5/2008 | Capote et al. |
| 2008/0140207 A1 | 6/2008 | Olmos et al. |
| 2008/0147194 A1 | 6/2008 | Grotz et al. |
| 2008/0161933 A1 | 7/2008 | Grotz et al. |
| 2008/0167657 A1 | 7/2008 | Greenhalgh |
| 2008/0183204 A1 | 7/2008 | Greenhalgh et al. |
| 2008/0221694 A1 | 9/2008 | Warnick et al. |
| 2008/0275455 A1 | 11/2008 | Berry et al. |
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0306488 A1 | 12/2008 | Altarac et al. |
| 2008/0319487 A1 | 12/2008 | Fielding et al. |
| 2008/0319549 A1 | 12/2008 | Greenhalgh et al. |
| 2009/0024217 A1 | 1/2009 | Levy et al. |
| 2009/0062833 A1 | 3/2009 | Song |
| 2009/0076616 A1 | 3/2009 | Duggal et al. |
| 2009/0125062 A1 | 5/2009 | Amin |
| 2009/0149956 A1 | 6/2009 | Greenhalgh et al. |
| 2009/0149959 A1 | 6/2009 | Conner et al. |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0265007 A1 | 10/2009 | Colleran |
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2009/0312763 A1 | 12/2009 | McCormack |
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0145455 A1 | 6/2010 | Simpson et al. |
| 2010/0160984 A1 | 6/2010 | Berry et al. |
| 2010/0179657 A1 | 7/2010 | Greenhalgh et al. |
| 2010/0211176 A1 | 8/2010 | Greenhalgh |
| 2010/0222816 A1 | 9/2010 | Gabelberger et al. |
| 2010/0286783 A1 | 11/2010 | Lechmann et al. |
| 2011/0035011 A1 | 2/2011 | Cain |
| 2011/0093074 A1 | 4/2011 | Glerum et al. |
| 2011/0160861 A1 | 6/2011 | Jimenez et al. |
| 2011/0172774 A1 | 7/2011 | Varela |
| 2011/0178599 A1 | 7/2011 | Brett |
| 2011/0276142 A1 | 11/2011 | Niemiec et al. |
| 2011/0301713 A1 | 12/2011 | Theofilos |
| 2011/0319997 A1 | 12/2011 | Glerum et al. |
| 2012/0035729 A1 | 2/2012 | Glerum et al. |
| 2012/0059470 A1 | 3/2012 | Weiman |
| 2012/0059472 A1 | 3/2012 | Weiman |
| 2012/0078371 A1 | 3/2012 | Gamache et al. |
| 2012/0109308 A1 | 5/2012 | Lechmann et al. |
| 2012/0130496 A1 | 5/2012 | Duffield et al. |
| 2012/0150229 A1 | 6/2012 | Hess |
| 2012/0165945 A1 | 6/2012 | Hansell et al. |
| 2012/0185049 A1 | 7/2012 | Varela |
| 2012/0209386 A1 | 8/2012 | Triplett et al. |
| 2012/0215313 A1 | 8/2012 | Saidha et al. |
| 2012/0226357 A1 | 9/2012 | Varela |
| 2012/0265309 A1 | 10/2012 | Glerum et al. |
| 2012/0277861 A1 | 11/2012 | Steele et al. |
| 2012/0277870 A1 | 11/2012 | Wolters et al. |
| 2012/0323329 A1 | 12/2012 | Jimenez et al. |
| 2012/0330426 A1 | 12/2012 | McLaughlin et al. |
| 2013/0023993 A1 | 1/2013 | Weiman |
| 2013/0023994 A1 | 1/2013 | Glerum |
| 2013/0150968 A1 | 6/2013 | Dinville et al. |
| 2013/0158663 A1 | 6/2013 | Miller et al. |
| 2013/0158669 A1 | 6/2013 | Sungarian et al. |
| 2013/0197647 A1 | 8/2013 | Wolters et al. |
| 2013/0211526 A1 | 8/2013 | Alheidt et al. |
| 2013/0226300 A1 | 8/2013 | Chataigner et al. |
| 2013/0245767 A1 | 9/2013 | Lee et al. |
| 2013/0274883 A1 | 10/2013 | McLuen et al. |
| 2014/0067071 A1 | 3/2014 | Weiman et al. |
| 2014/0088711 A1 | 3/2014 | Chin et al. |
| 2014/0088714 A1 | 3/2014 | Miller et al. |
| 2014/0100662 A1 | 4/2014 | Patterson et al. |
| 2014/0163683 A1 | 6/2014 | Seifert et al. |
| 2014/0180417 A1 | 6/2014 | Bergey |
| 2015/0051702 A1 | 2/2015 | Chataigner et al. |
| 2015/0057754 A1 | 2/2015 | Reed et al. |
| 2015/0066145 A1 | 3/2015 | Rogers et al. |
| 2015/0088258 A1 | 3/2015 | Jimenez et al. |
| 2015/0127107 A1 | 5/2015 | Kim et al. |
| 2015/0134064 A1 | 5/2015 | Grotz et al. |
| 2015/0209089 A1 | 7/2015 | Chataigner et al. |
| 2015/0216676 A1 | 8/2015 | Shulock et al. |
| 2015/0289988 A1 | 10/2015 | Ashley et al. |
| 2015/0305887 A1 | 10/2015 | McAtamney et al. |
| 2015/0320568 A1* | 11/2015 | Ameil ............... A61F 2/4455 623/17.13 |
| 2015/0374508 A1 | 12/2015 | Sandul |
| 2016/0166396 A1 | 6/2016 | McClintock |
| 2016/0324654 A1 | 11/2016 | Loebl et al. |
| 2016/0338845 A1 | 11/2016 | Ashleigh |
| 2017/0100258 A1 | 4/2017 | Jimenez et al. |
| 2017/0119543 A1 | 5/2017 | Dietzel et al. |

FOREIGN PATENT DOCUMENTS

| | | |
|---|---|---|
| DE | 4012622 C1 | 7/1991 |
| DE | 4327054 C1 | 4/1995 |
| EP | 0576379 B1 | 6/1993 |
| EP | 0610837 B1 | 7/1994 |
| EP | 1378202 A1 | 1/2004 |
| EP | 3111896 A1 | 1/2017 |
| FR | 2794968 A1 | 12/2000 |
| JP | 2000-513263 A | 10/2000 |
| JP | 2013516206 A | 5/2013 |
| JP | 2015501189 A | 1/2015 |
| JP | 2015054235 A | 3/2015 |
| JP | 2015507989 A | 3/2015 |
| JP | 2015510817 A | 4/2015 |
| KR | 200290058 Y1 | 9/2002 |
| SU | 1424826 A1 | 9/1988 |
| WO | 9201428 A1 | 2/1992 |
| WO | 9525485 A1 | 9/1995 |
| WO | 9942062 A1 | 8/1999 |
| WO | 1999042062 A1 | 8/1999 |
| WO | 1999066867 A1 | 12/1999 |
| WO | 2002045625 A1 | 6/2002 |
| WO | 2004019829 A1 | 3/2004 |
| WO | 2004069033 A2 | 8/2004 |
| WO | 2006045094 A2 | 4/2006 |
| WO | 2006047587 A2 | 5/2006 |
| WO | 2006113080 A2 | 10/2006 |
| WO | 2008044057 A1 | 4/2008 |
| WO | 2008134515 A1 | 11/2008 |
| WO | 2009114381 A1 | 9/2009 |
| WO | 2010103344 A1 | 9/2010 |
| WO | 2012031267 A1 | 3/2012 |
| WO | 2012117312 A2 | 9/2012 |
| WO | 2014047612 A1 | 3/2014 |
| WO | 2015009793 A1 | 1/2015 |
| WO | 2015164707 A1 | 10/2015 |

* cited by examiner

DEVICE AND METHOD FOR DEPLOYMENT OF AN ANCHORING DEVICE FOR INTERVERTEBRAL SPINAL FUSION

CROSS-REFERENCE TO RELATED APPLICATIONS

This patent application is a continuation of U.S. patent application Ser. No. 16/458,909 filed on Jul. 1, 2019, which is a divisional of U.S. patent application Ser. No. 14/718,514 filed on May 21, 2015, which is incorporated in its entirety herein.

FIELD OF THE INVENTION

The present invention relates generally to intervertebral spacers for fusing adjacent vertebras, and more particularly to a device and methods for doing so.

BACKGROUND

Intervertebral spinal fusion is well known in the art. In the prior art, an intervertebral spacer is implanted between two adjacent intervertebral bodies. The spacer allows a surgeon to deposit bone graft between the problem vertebras in order to fuse the vertebras together. To achieve proper fusion, the implanted spacer must be securely anchored between the vertebras such that there is little to no movement once implanted. Protrusions arranged on the superior and inferior surfaces of the spacer provides a means to stabilize the spacer between the vertebras. However, it has been discovered that spacers stabilized in this way may still move due to the stress exerted on the implanted spacer when the patient moves. Other commonly employed stabilizing techniques include pedicle screws and rods. In this technique, pedicle screws are independently screwed into two or three spine segments. A short rod is then used to connect the pedicle screws to prevent motion at the segments that are being fused. However, this technique is time consuming because the pedicle screws need to be independently screwed into the vertebras. It also requires the surgeon to make large/numerous incisions in the patient to insert the pedicle screws. Because of these deficiencies in the prior art, there exists a need to provide a more effective and efficient way of stabilizing adjacent vertebras in the field of intervertebral spinal fusion.

SUMMARY

For the purpose of the following description and the appended claims, "proximal" and its inflected forms are defined as the part, portion, section, etc., of an object that is closest to the person using that object.

For the purpose of the following description and the appended claims, "distal" and its inflected forms are defined as the part, portion, section, etc., of an object that is furthest away to the person using that object.

The present invention provides a way to stabilize adjacent vertebras without some of the deficiencies of the prior art discussed above. In the illustrative embodiment of the present invention, a spacer is provide with an upper guide and a lower guide. The upper and lower guides are adapted to guide the simultaneous deployment of a respective upper anchor and lower anchor of an anchoring device when force is applied thereto. More precisely, force is simultaneously applied to a proximal portion of the upper and lower anchors. The force simultaneously deploys the upper and lower anchors into their respective intervertebral bodies. The upper and lower anchors are constructed and dimensioned in such a way to pierce and penetrate into their respective vertebras. The combination of the anchors and the protrusions arranged on the surfaces of the spacer provides additional stabilization of the implanted spacer. These advantages of the present invention will be apparent from the following disclosure and the appended claims.

DETAILED DESCRIPTION

Figure 1A:
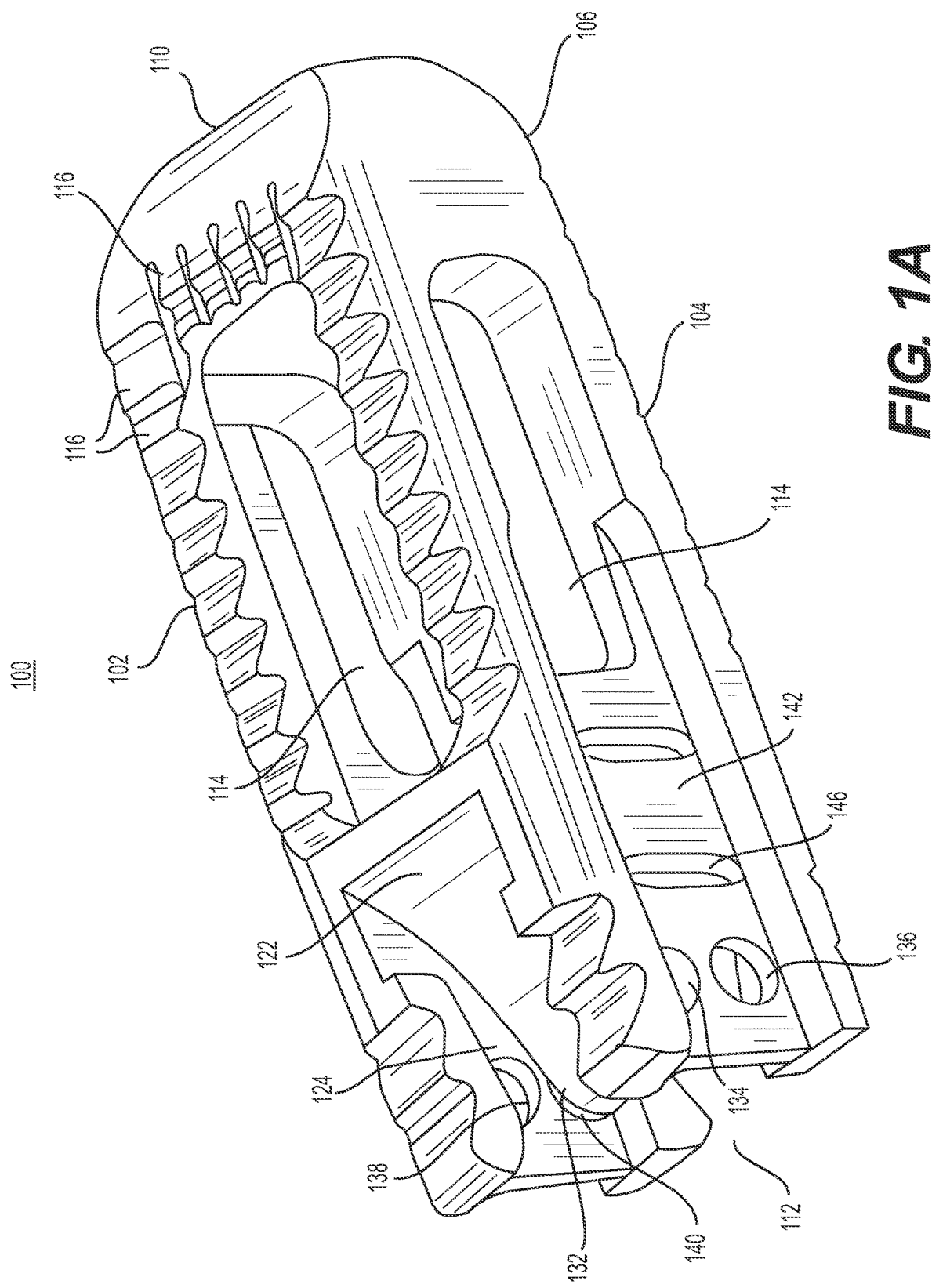
FIG. 1A depicts a perspective view of an intervertebral spacer in accordance with an illustrative embodiment of the present invention.
Figure 1B:
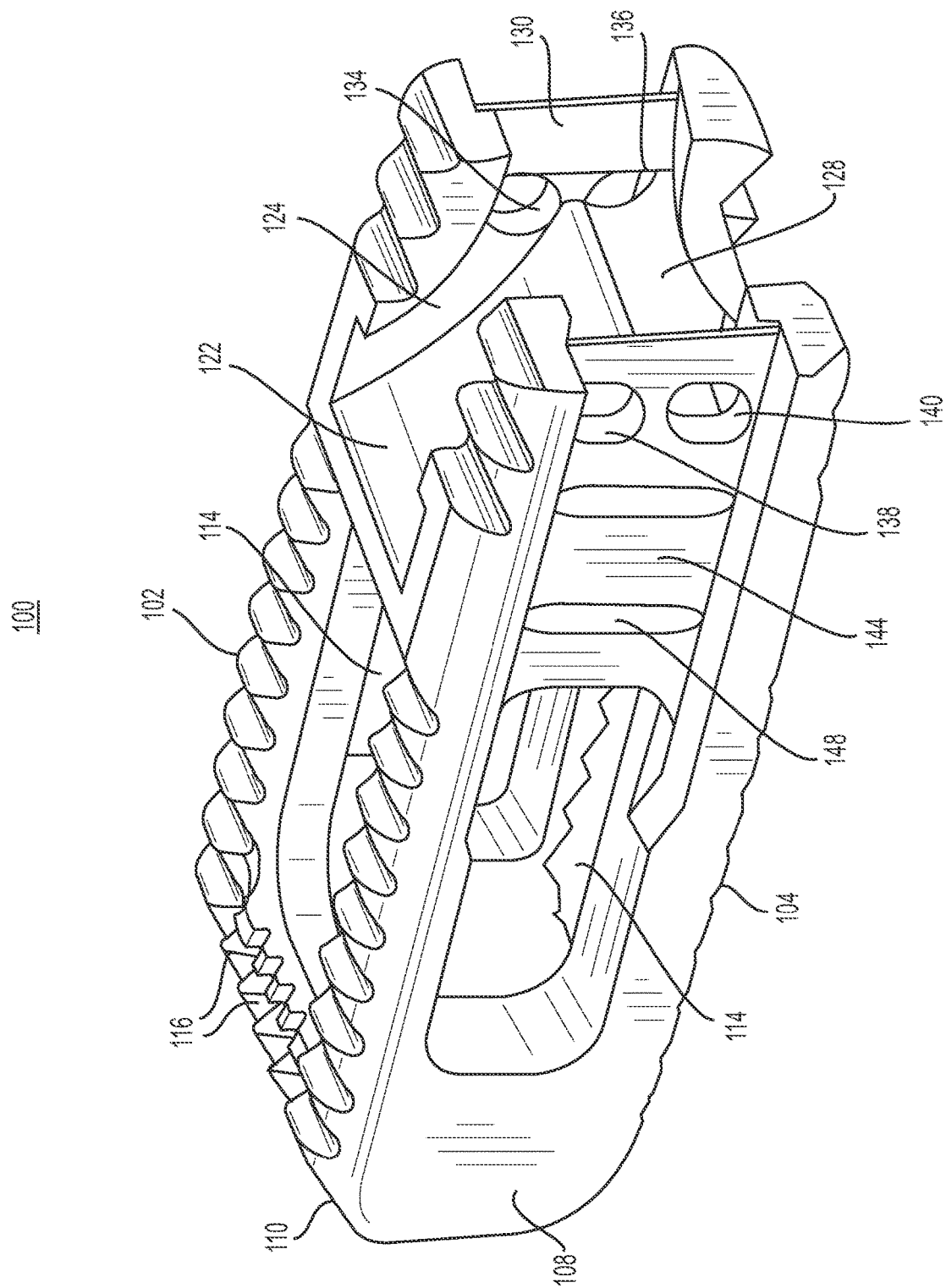
FIG. 1B depicts another perspective view of the intervertebral spacer of FIG. 1A.

FIGS. 1A and 1B depict perspective views of intervertebral spacer 100 in accordance with an illustrative embodiment of the present invention. Spacer 100 generally has a rectangular shape, but the present invention is not limited to such a shape. Spacer 100 can have any shape, size, or combination thereof to meet the needs of a spinal fusion candidate.

As depicted in FIGS. 1A and 1B, spacer 100 comprises superior surface 102, inferior surface 104, lateral surfaces 106 and 108, distal portion 110, and proximal portion 112. Inferior surface 104 is a mirror image of superior surface 102 and lateral surface 108 is a mirror image of lateral surface 106. Spacer 100 is preferably formed from titanium alloy but other biocompatible materials (e.g., polyetheretherketone (PEEK), other surgical grade metals, alloys, or a combination thereof) can also be used to form spacer 100.

Beginning at distal portion 110, spacer 100 is constructed to have a tapered end that narrows towards the distal most end. This design helps facilitate easier entry of spacer 100 into the narrow disc space arranged between two adjacent vertebral bodies.

Figure 2A:
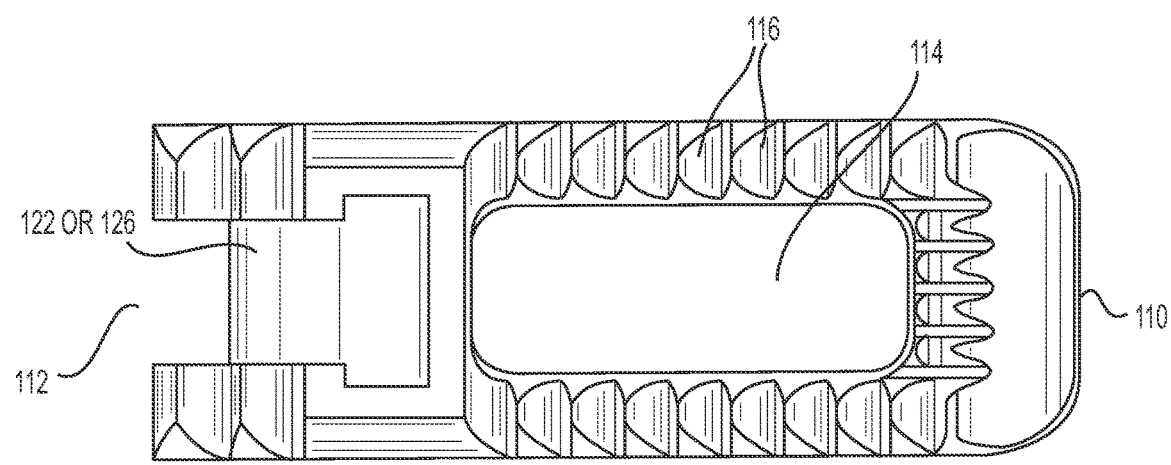
FIG. 2A depicts a top view of the intervertebral spacer of FIGS. 1A and 1B.
Figure 2B:
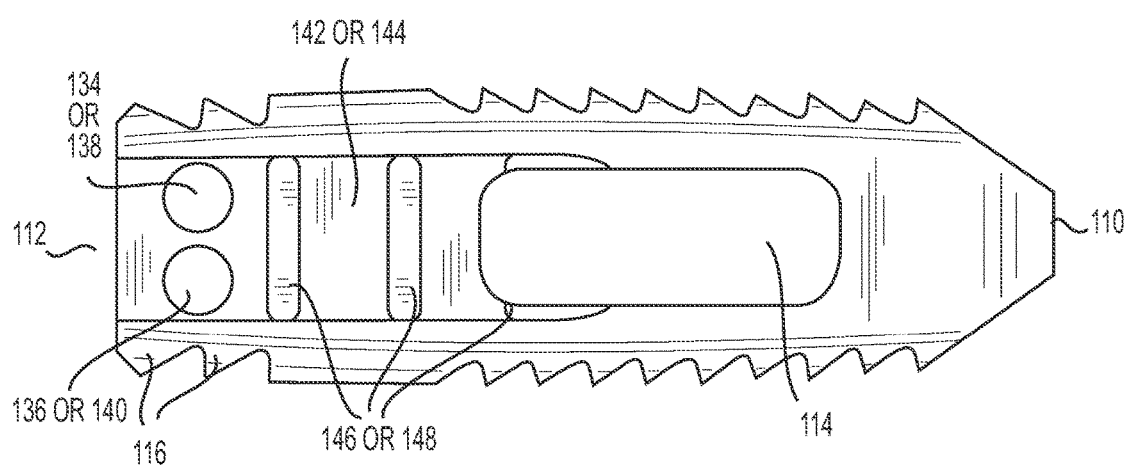
FIG. 2B depicts a side view of the intervertebral spacer of FIGS. 1A and 1B.

To fuse the adjacent vertebras together, bone graft is used. For this purpose, the body of spacer 100 is provided with through-hole 114. The through-hole extends through the center of surfaces 102, 104, 106, and 108 and is adapted to receive the bone graft for fusing the adjacent vertebras. In the illustrative embodiment, through-hole 114 generally has a rectangular shape. However, those skilled in the art will appreciate after reading this disclosure that through-hole 114 can have any shape, size, or a combination thereof. As further depicted in FIGS. 1A and 1B, surfaces 102 and 104 are provided with a plurality of protrusions or teeth 116 to help prevent spacer 100 from expulsion after being implanted between the adjacent vertebras. It will be appreciated by those skilled in the art, after reading this disclosure, that teeth 116 can be angled in any number of degrees (e.g., 45°, 90°, etc.) and can have any number of orientations without departing from the scope of the present invention. Through-hole 114 and teeth 116 can be seen more clearly in FIGS. 2A and 2B.

Turning now to proximal portion 112, upper and lower guides are provided to respectively guide the deployment of upper anchor 118 and lower anchor 120 into their respective vertebral bodies. The upper and lower anchors will be discussed in more detail below, with respect to FIGS. 3A and 3B. In the illustrative embodiment, the upper guide is characterized by an upper inclined surface 122 (e.g., a curvilinear surface, etc.) and an upper pair of oppositely positioned lateral recesses 124. Because the lower guide is a mirror image of the upper guide, the lower guide is also characterized by a lower inclined surface 126 and a lower pair of oppositely positioned lateral recesses 128. The upper and lower pair of lateral recesses 124 and 128 are dimensioned to respectively complement the arc, curvature, etc., of the upper and lower anchors. An advantage of recesses 124 and 128 is that they ensure that their respective anchors maintain a desired trajectory when impacted by an anchor driver. The recesses 124 and 128 also prevent their respective anchors from egressing out of spacer 100 when impacted by the anchor driver. These features and their advantages will be discussed in more detail below, with reference to FIGS. 4A and 4B.

Proximal portion 112 also comprises a pair of oppositely positioned lateral chamfers 130 and 132. Each of the lateral chamfers has a sloping edge and is positioned proximally to their respective locking recesses 134, 136, 138, and 140. As will be described in more detail below, with reference to FIGS. 6A-6D, the chamfer-recess combination is a mechanism that allows upper anchor 118 and lower anchor 120 to be locked to spacer 100 after deployment. It will be appreciated by those skilled in the art, after reading this disclosure, that locking recesses 134, 136, 138, 140 could be detents in some embodiments and through-holes in other embodiments.

Proximal portion 112 further comprises lateral surfaces 142 and 144 that are respectively constructed with gripper recesses 146 and 148. The gripper recesses are dimensioned and arranged to receive corresponding ribs of an implantation instrument employed by a surgeon. The ribs are adapted to fit squarely into their corresponding recesses so that spacer 100 can be securely gripped by the surgeon. It should be noted that gripping the spacer with an implantation instrument serves at least two purposes. First, it enables the surgeon to more easily orient spacer 100 in a desired position within the narrow disc space of the adjacent vertebras. Secondly, it prevents spacer 100 from coming free from the implantation instrument while the surgeon is impacting the upper and lower anchors with an anchor driver. Although each of the lateral surfaces is depicted as having three gripping recesses, it will be appreciated by those skilled in the art that each of the lateral surfaces can have more or less gripper recesses than depicted. This feature of the present invention will be described in more detail below, with reference to FIGS. 5A-5D.

Figure 3A:
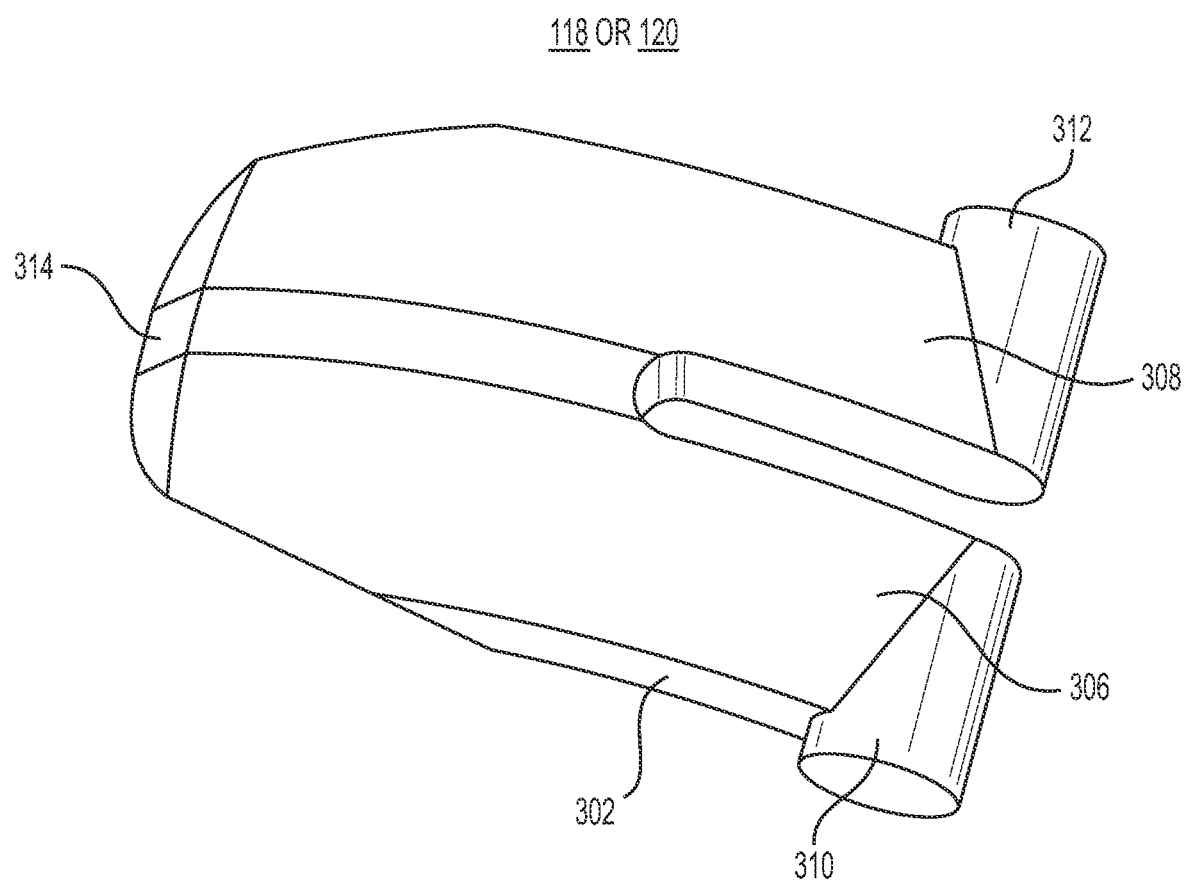
FIG. 3A depicts one side of an anchor in accordance with an illustrative embodiment of the present invention.
Figure 3B:
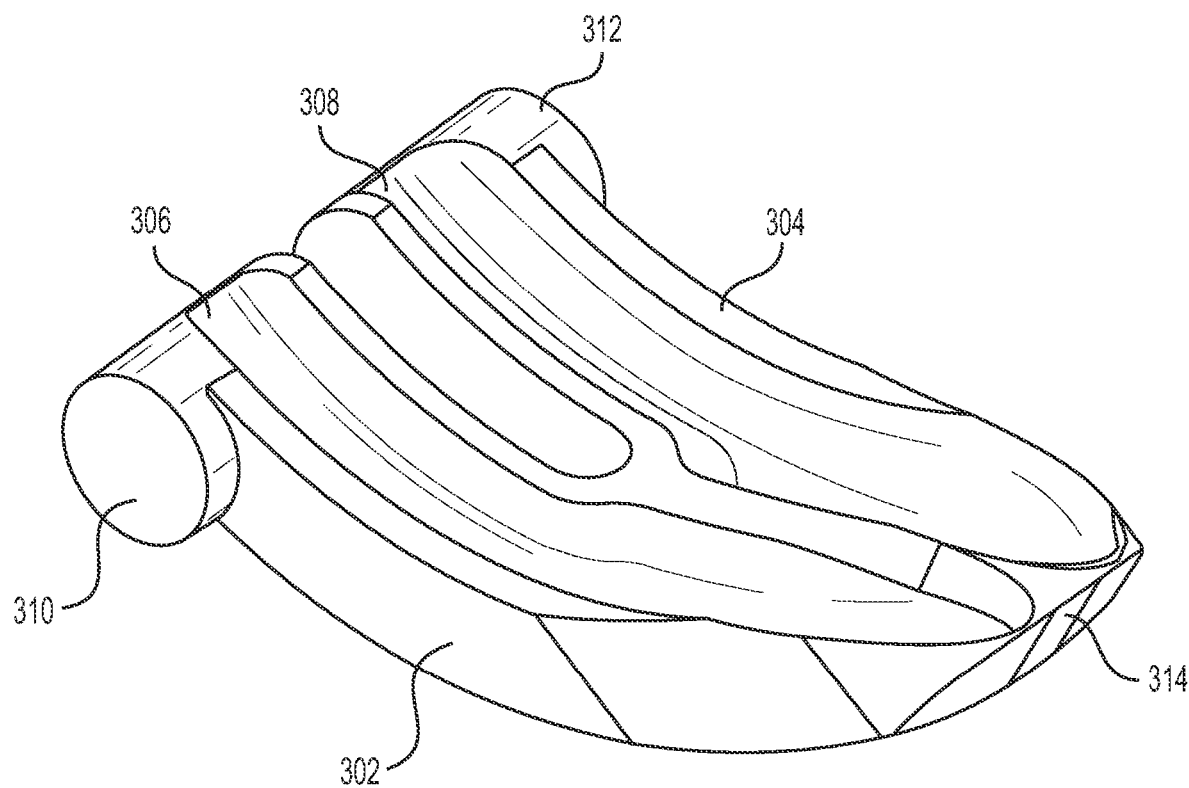
FIG. 3B depicts the other side of the anchor of FIG. 3A.

FIGS. 3A and 3B are perspective views of an anchor in accordance with an illustrative embodiment of the present invention. Since upper anchor 118 and lower anchor 120 have substantially the same physical and functional characteristics, thus being interchangeable, the following discussion of FIGS. 3A and 3B will use the word "anchor" to describe both the upper and lower anchors. Further, it should be noted that upper anchor 118 and lower anchor 120 (whether formed as independent pieces or as a single unitary piece) collectively define an anchoring device.

FIG. 3A depicts the surface of an anchor that is adapted to slide along an inclined surface of a guide (e.g., upper inclined surface 122 or lower inclined surface 126). In the illustrative embodiment, the anchor is constructed to have a curved or semi-curved surface that is contoured to be substantially the same as the inclined surface of the guide it slides on. The surface of the anchor is preferably smooth throughout its length in order to reduce the amount of friction drag produced when the surface slides along the inclined surface.

The anchor also comprises a pair of oppositely positioned lateral sides 302 and 304, which are adapted to slide into their respective lateral recesses (e.g., upper lateral recesses 124 or lower lateral recesses 128). The anchor is also constructed with a pair of flexible prongs 306 and 308, which respectively comprises lateral projections 310 and 312. The flexible prongs and lateral projections work in cooperation to lock the anchor to spacer 100 in a deployed position. The lateral sides, flexible prongs, and lateral projections of the anchor are also depicted in FIG. 3B.

To enable the anchor to penetrate a vertebral body, distal portion 314 of the anchor is tapered to form an edge. Since the anchor is made of titanium alloy, the distal portion of the anchor is sufficiently strong to pierce and penetrate through the endplate of the vertebral body. Although the anchor is preferably formed from titanium alloy, other biocompatible materials (e.g., polyetheretherketone (PEEK), other surgical grade metals, alloys, or a combination thereof) can be used to form the anchor.

It will be clear to those skilled in the art that the foregoing discussion of FIGS. 3A and 3B applies to both upper anchor 118 and lower anchor 120.

Figure 4A:
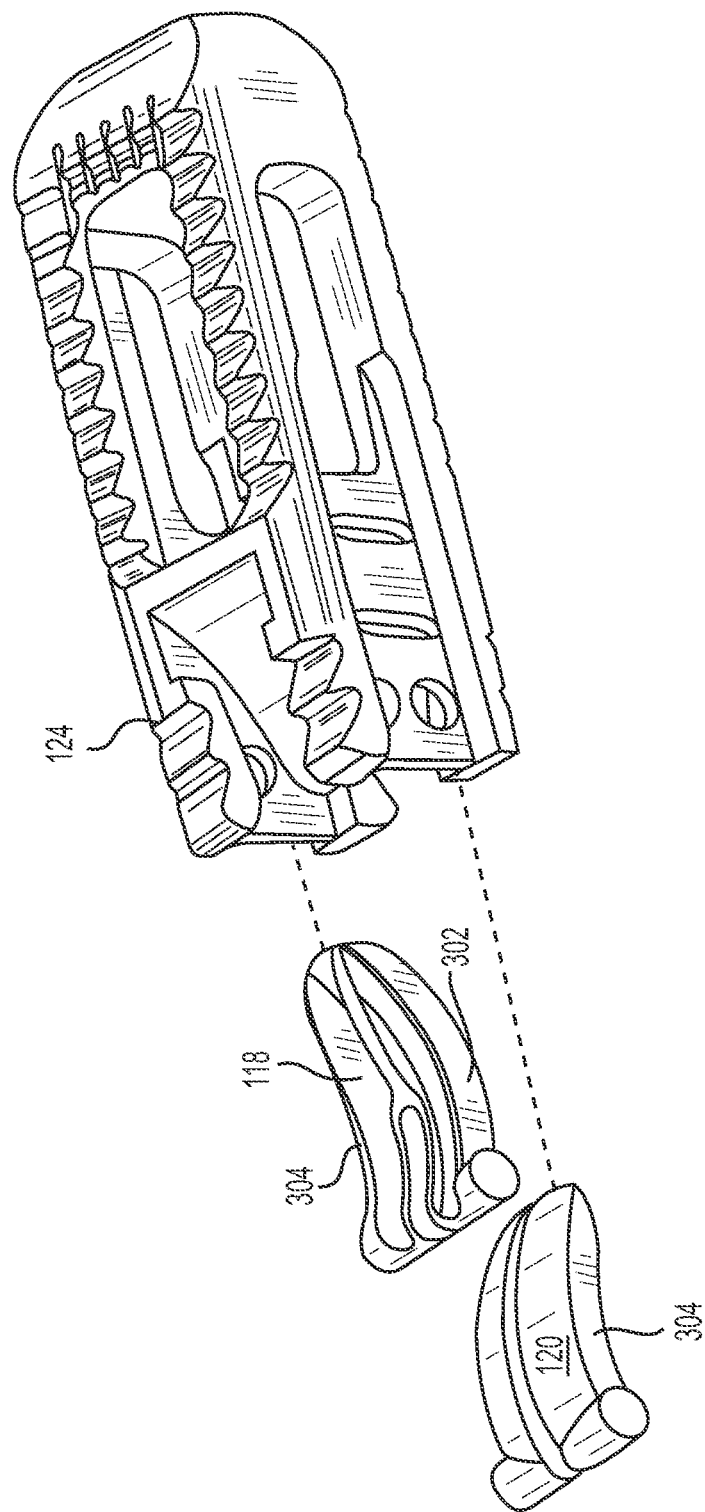
FIG. 4A depicts two anchors being loaded into the intervertebral spacer of FIGS. 1A and 1B.
Figure 4B:
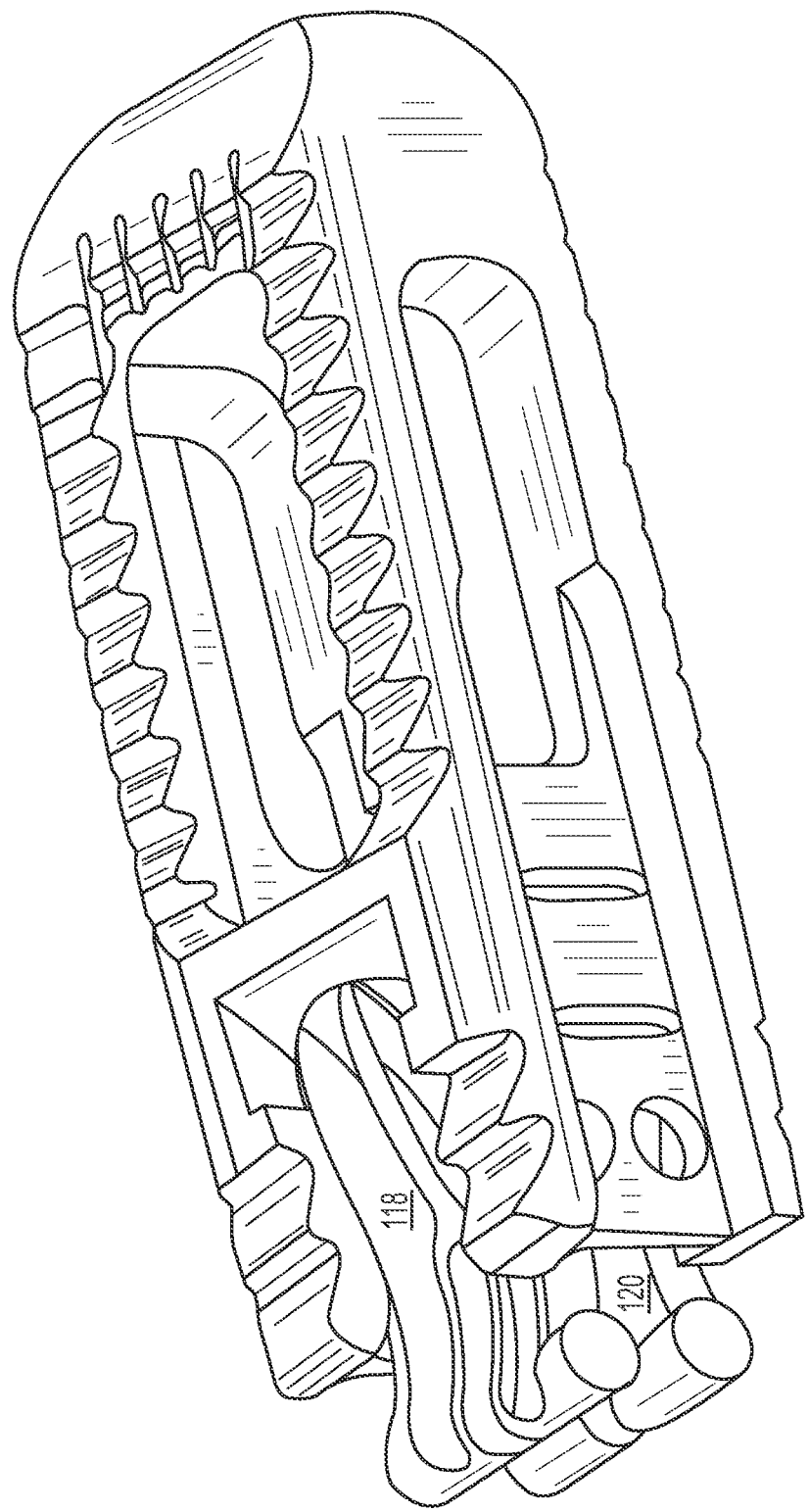
FIG. 4B depicts the two anchors of FIG. 4A loaded into the intervertebral spacer of FIGS. 1A and 1B, the two anchors being in an undeployed state.

FIG. 4A depicts upper anchor 118 and lower anchor 120 being loaded into spacer 100. As discussed above, the upper guide of spacer 100 has an upper pair of oppositely positioned lateral recesses 124. Each lateral recess 124 is adapted to receive a respective one of lateral sides 302 and 304 of upper anchor 118. Similarly, the lower guide of spacer 100 has a lower pair of oppositely positioned lateral recesses 128 (shown more clearly in FIG. 1B). Each lateral recess 128 is adapted to receive a respective one of lateral sides 302 and 304 of lower anchor 120. Turning now to FIG. 4B, this figure depicts spacer 100 loaded with the upper and lower anchors. In FIG. 4B, upper anchor 118 and lower anchor 120 are in an undeployed state and are disposed entirely within spacer 100. That is, no part of upper anchor 118 and lower anchor 120 extend beyond the profile of teeth 116 arranged on spacer 100. In the loaded/undeployed state, spacer 100 is ready to be gripped by an implantation instrument for simultaneous deployment into their respective intervertebral bodies.

Figure 5A:
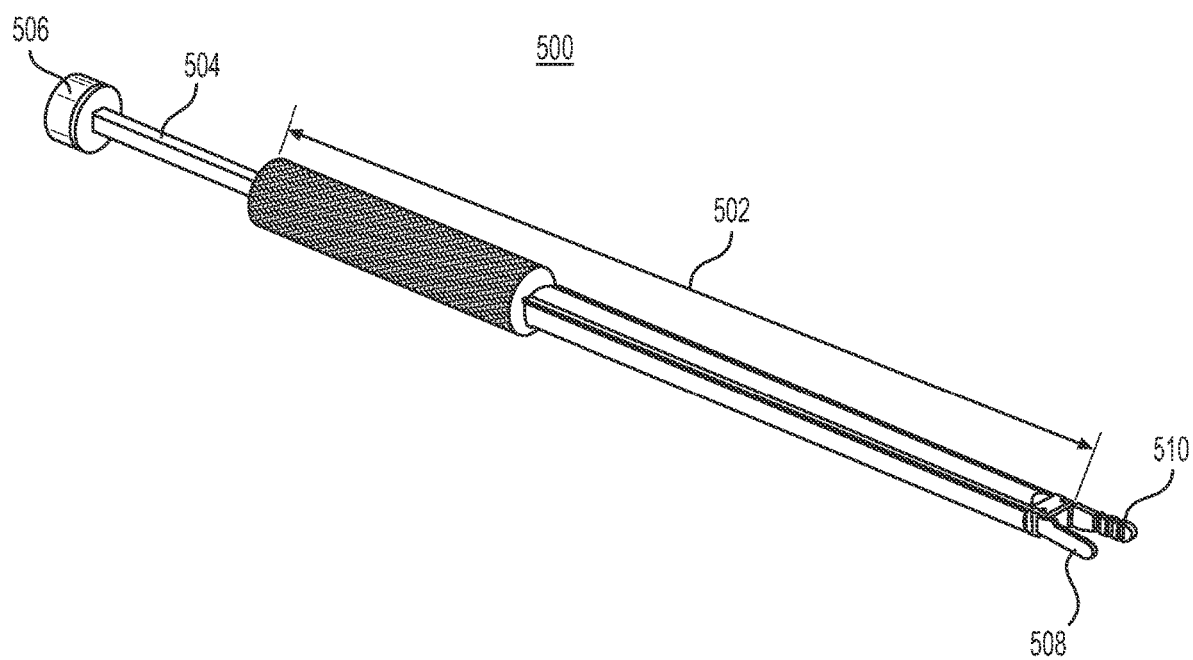
FIG. 5A depicts a perspective view of an implantation instrument in accordance with an illustrative embodiment of the present invention.

FIG. 5A is a perspective view of implantation instrument 500, which comprises, inter alia, housing 502, anchor driver 504, handle 506, and a pair of oppositely positioned grippers 508 and 510. As will be discussed in more detail below, with reference to FIGS. 5B-5D, anchor driver 504 can be advanced forwards or retracted backwards via handle 506 to respectively grip or release spacer 100.

Figure 5B:
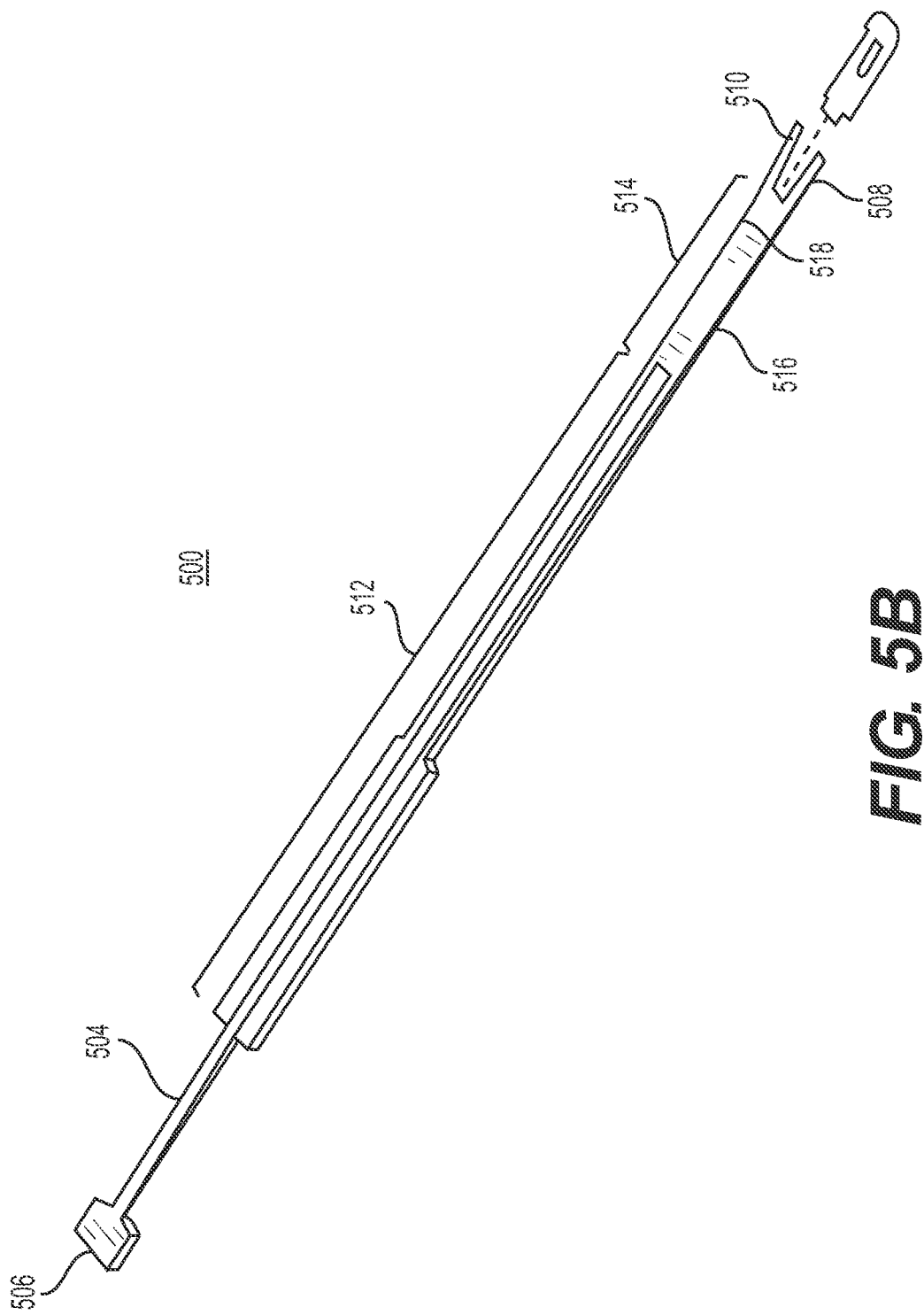
FIG. 5B depicts a cross-sectional view of the implantation instrument of FIG. 5A, the cross-sectional view depicting a narrower section and a wider section of the implantation instrument.

FIG. 5B is a cross-sectional view of the implantation instrument of FIG. 5A. As shown in this view, housing 502 is divided into two sections—namely, a narrower section 512 and a wider section 514. Anchor driver 504 is constructed to fit squarely into narrower section 512 with little or no lateral and radial movement, while the area of wider section 514 is dimensioned to accommodate the width of anchor driver 504 and a pair of adjacently positioned, oppositely bowed leaf springs 516 and 518.

In the configuration depicted in FIG. 5B, anchor driver 504 can be advanced forwards towards leaf springs 516 and 518 via handle 506. As the forward advancement causes anchor driver 504 to be wedged between leaf springs 516 and 518, their respective grippers 508 and 510 will begin to simultaneously pivot inward to clamp onto the lateral surfaces of spacer 100.

Figure 5C:
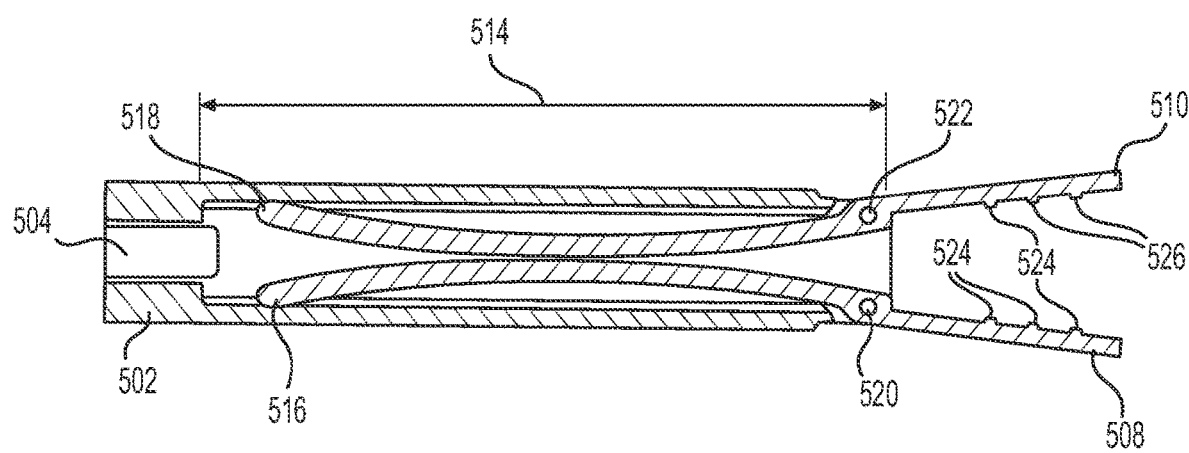
FIG. 5C depicts an exploded, cross-sectional view of the wider section of the implantation instrument of FIG. 5A.

More precisely, and with reference to FIG. 5C, the forward advancement of anchor driver 504 causes gripper 508 to pivot inwardly about pivot point 520. This pivot action is a result of leaf spring 516 being compressed outwards towards the wall of housing 502 as anchor driver 504 engages the bowed portion of leaf spring 516. As gripper 508 pivots inwards, ribs 524 engage their respective gripper recess 146 (depicted in FIG. 1A) arranged on spacer 100. Likewise, gripper 510 will pivot inwardly about pivot point 522 in response to the forward advancement of the driver, resulting in ribs 526 engaging their respective gripper recess 148 (depicted in FIG. 1B). By means of the foregoing, spacer 100 can be securely gripped by implantation instrument 500, as depicted in FIG. 5D.

Figure 5D:
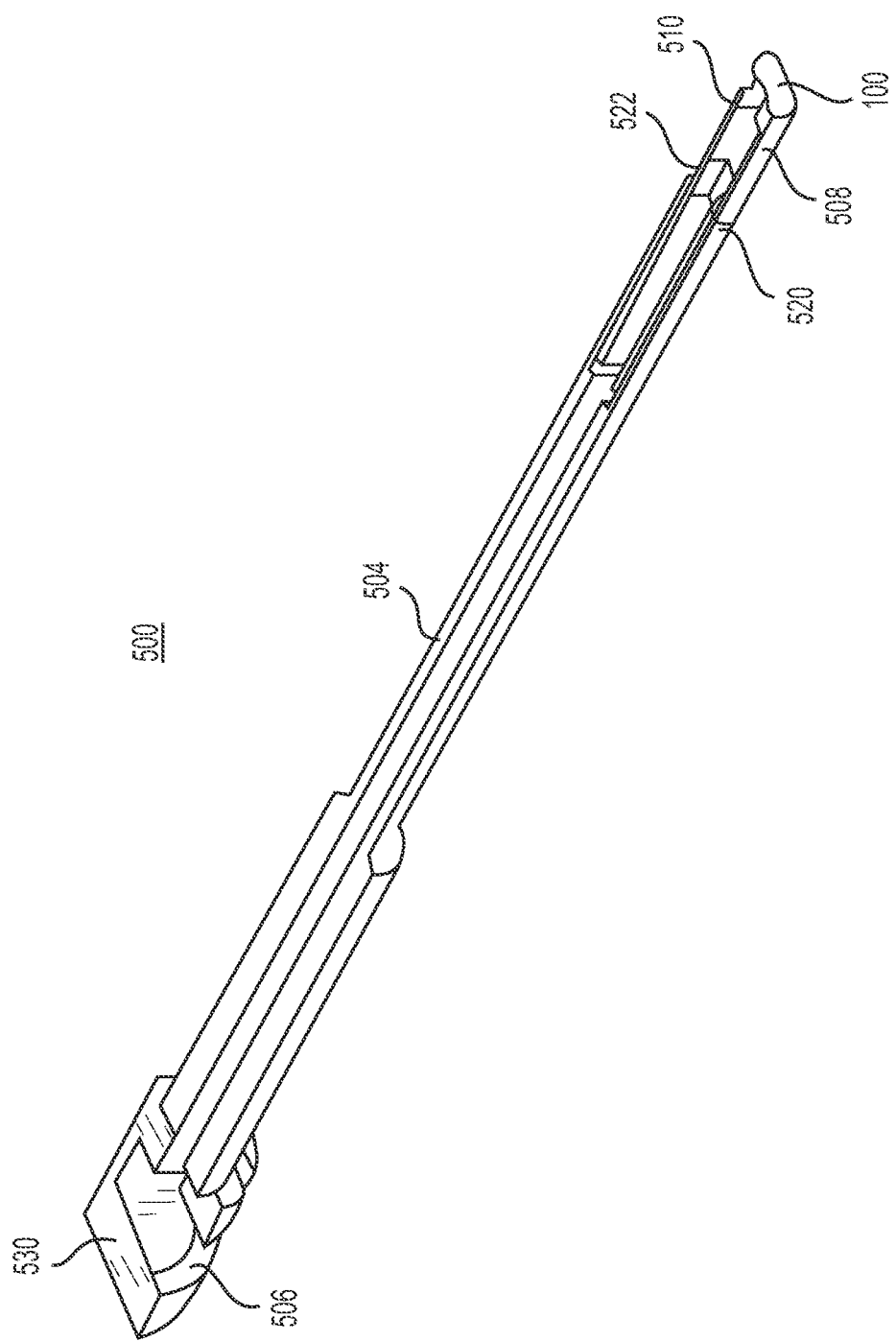
FIG. 5D depicts a cross-sectional view of the implantation instrument gripping the lateral surfaces of the intervertebral spacer of FIGS. 1A and 1B.

As depicted in FIG. 5D, the head of anchor driver 504 stops at or slightly before the distal end of housing 502 after gripping spacer 100. While spacer 100 is being gripped by implantation instrument 500, spacer 100 is positioned within the narrow disc space between adjacent vertebras. Continuing to grip spacer 100 with implantation instrument 500, the surgeon removes cap 530 and is now ready to impact handle 506 with a weighted object (e.g., hammer, mallet, etc.). In accordance with the illustrative embodiment, cap 530 has two functionalities. First, cap 530 when attached to handle 506 disallows forward movement of anchor driver 504 past a certain point—namely, the distal end of housing 502. Secondly, cap 530 prevents inadvertent deployment of upper anchor 118 and lower anchor 120 during positioning of spacer 100 within the adjacent vertebral bodies.

When the surgeon impacts handle 506 with a weighted object, anchor driver 504 is driven forwards into the proximal portion of upper anchor 118 and lower anchor 120, thereby simultaneously deploying the anchors into their respective vertebras. The surgeon may impact handle 506 one or more times so that the anchors reach a desired depth within their vertebras, and so that the anchors engage the locking feature of the present invention described in more detail below. Once upper anchor 118 and lower anchor 120 is locked to spacer 100 in the deployed position, the surgeon can retract anchor driver 502 so that leaf springs 516 and 518 can return to their relaxed state. While returning to their relaxed state, grippers 508 and 510 will begin to pivot outwardly to disengage from their gripper recesses, thereby releasing spacer 100.

Figure 6A:
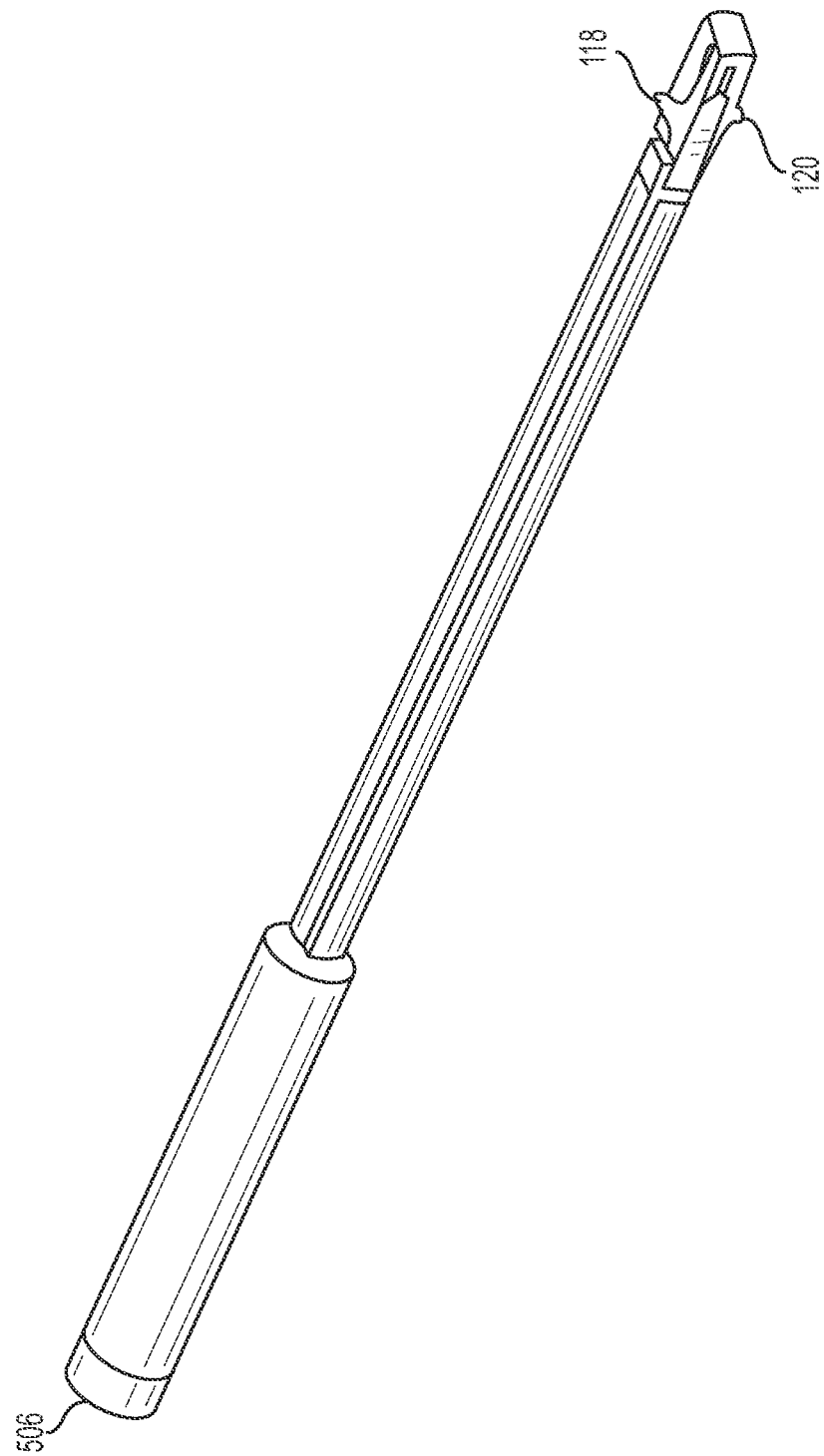
FIG. 6A depicts the implantation instrument of FIG. 5A having deployed the anchors of FIG. 4A.
Figure 6B:
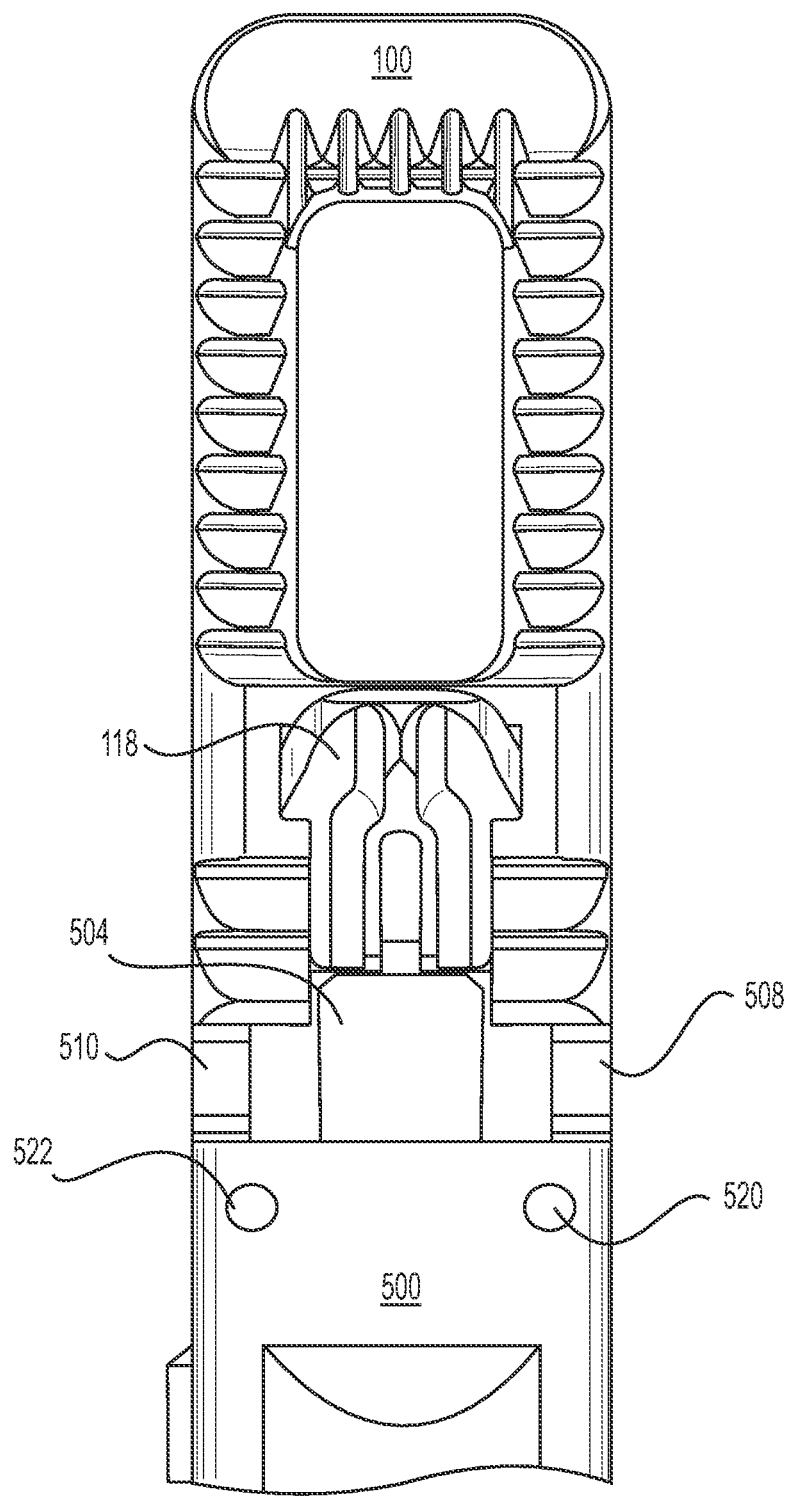
FIG. 6B depicts an exploded, top view of the deployed anchors of FIG. 6A.
Figure 6C:
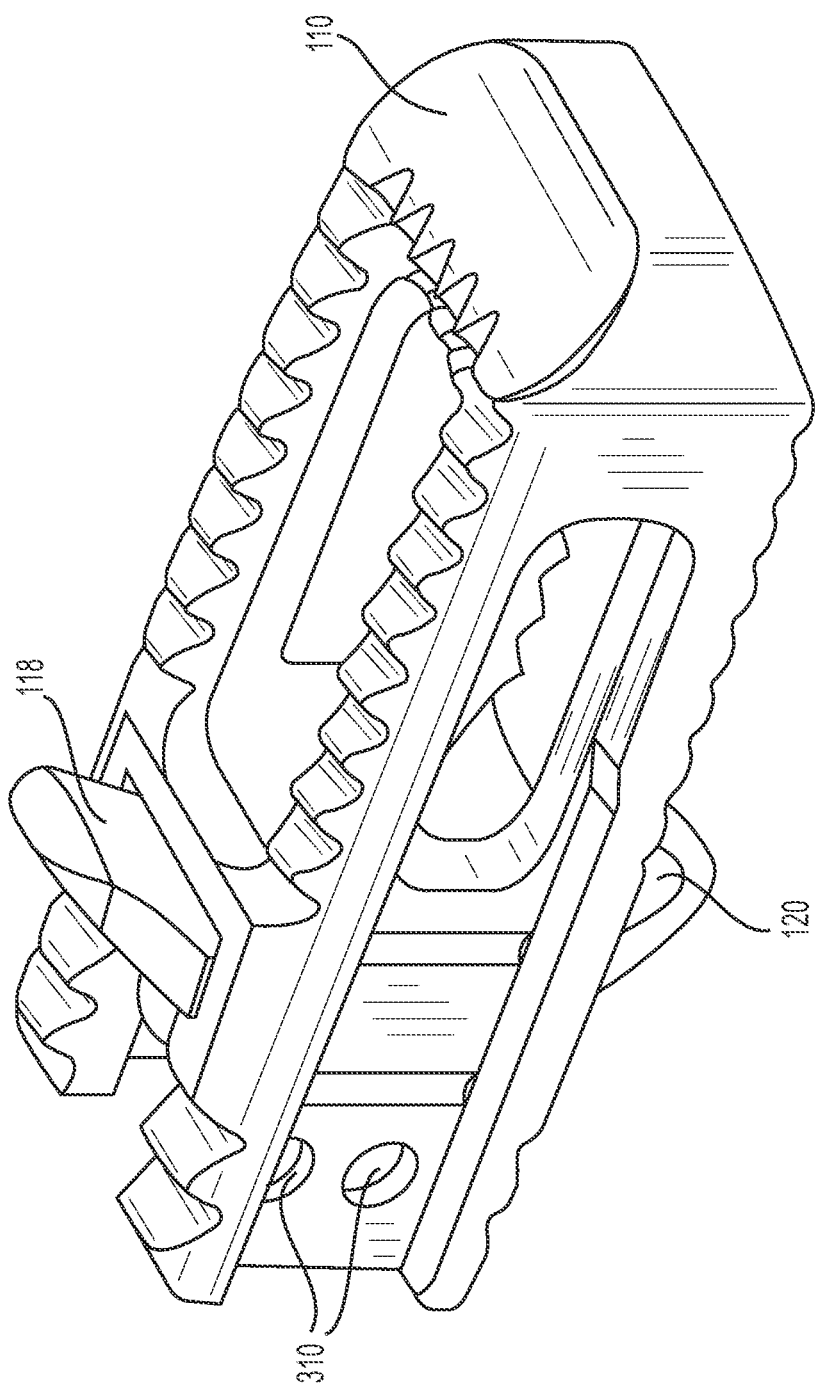
FIGS. 6C and 6D depict an exploded, perspective view of the deployed anchors of FIG. 6A.
Figure 6D:
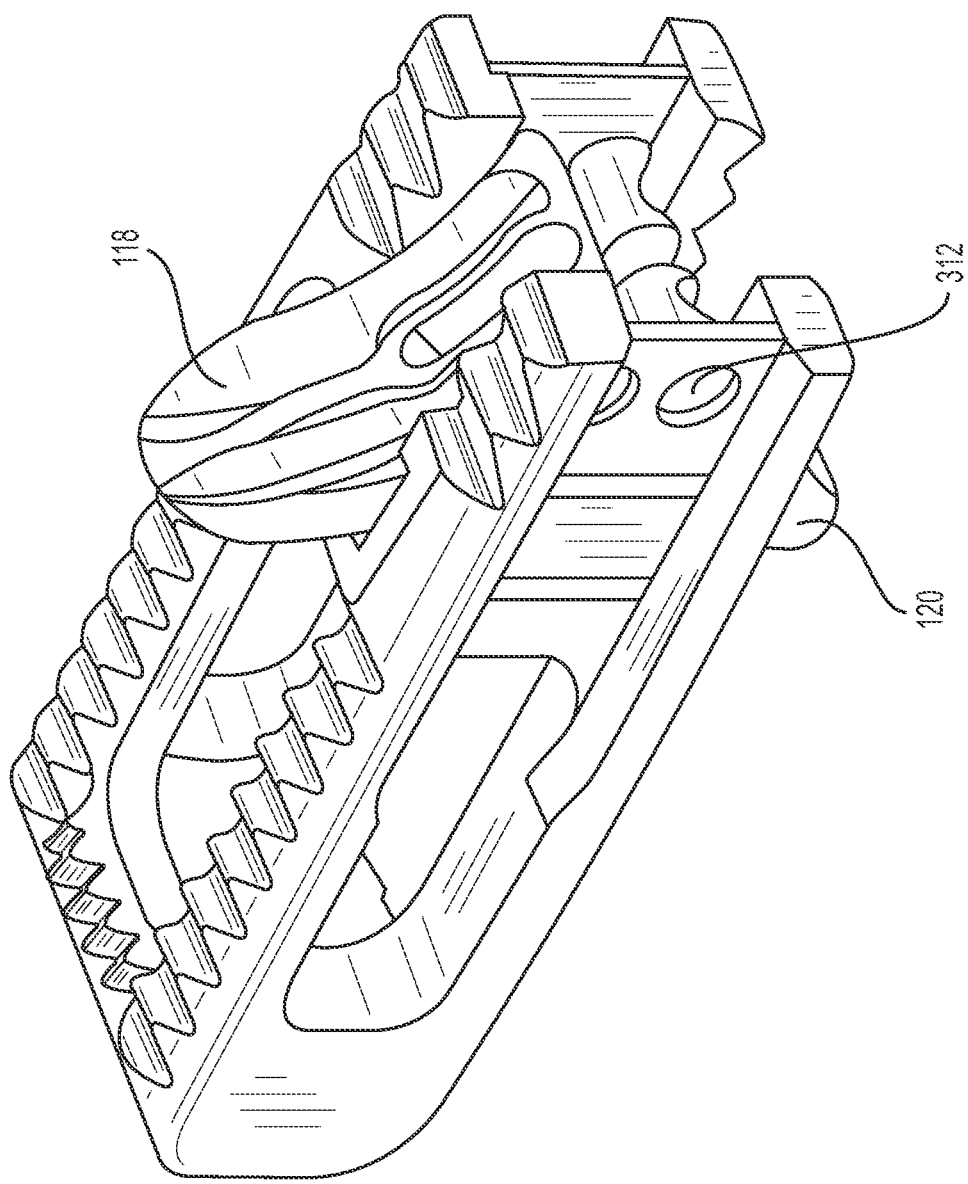

FIG. 6A depicts a perspective view of implantation instrument 500 in which driver anchor 504 has simultaneously deployed upper anchor 118 and lower anchor 120. As discussed above, the head of anchor driver 504 is simultaneously driven into the proximal portion of upper anchor 118 and lower anchor 120 as the surgeon impacts handle 506. This causes both the upper anchor 118 and lower anchor 120 to independently slide along the upper inclined surface 122 and lower inclined surface 126, respectively. The upper and lower inclined surfaces respectively press against the surface of the upper and lower anchors (i.e., the surface depicted in FIG. 3A) to deploy the anchors into their respective vertebral bodies. FIGS. 6B-6D depict upper anchor 118 and lower anchor 120 simultaneously deployed after being impacted by anchor driver 504. As shown in these figures, the distal ends of upper anchor 118 and lower anchor 120 in the deployed state are radially extended outside of spacer 100. That is, the distal ends of upper anchor 118 and lower anchor 120 extend past the height of teeth 116 of spacer 100 after being deployed.

From the foregoing discussion, it will be clear to those skilled in the art that upper anchor 118 and lower anchor 120 are separate elements that slide independently of each other along their respective upper and lower guides. It will also be clear from the foregoing discussion that an advantage of using the upper and lower anchors of the present invention is that they provide additional anchorage for stabilizing a spacer. In other words, not only is the spacer anchored to the intervertebral bodies via its teeth, the spacer is also provided with additional anchorage by the upper and lower anchors, since they extend past the profile of the teeth and therefore penetrating deeper into the intervertebral bodies.

Returning to FIGS. 6C and 6D, these figures depict upper anchor 118 and lower anchor 120 locked to spacer 100 in a deployed position. Since upper anchor 118 and lower anchor 120 are locked to spacer 100 in substantially the same way, the following discussion of FIGS. 6C and 6D will use the word "anchor" to describe both the upper and lower anchors.

As the anchor is impacted by driver 504, lateral projections 310 and 312 will respectively engage the sloping edge of lateral chamfers 130 and 132. Lateral chamfers 130 and 132 are depicted in the figures as being arranged proximally to locking recesses 134, 136, 138, and 140 of spacer 100. The pressure and force of the impact causes flexible prongs 306 and 308 to flex laterally inwardly. As lateral projections 310 and 312 past their respective lateral chamfers, flexible prongs 306 and 308 will return to a relaxed state, thereby causing lateral projections 310 and 312 to laterally extend into their corresponding locking recess 134, 136, 138, and 140. This locking feature of the present invention prevents the anchors from disengaging from spacer 100 after being deployed into the vertebral bodies.

Figure 7A:
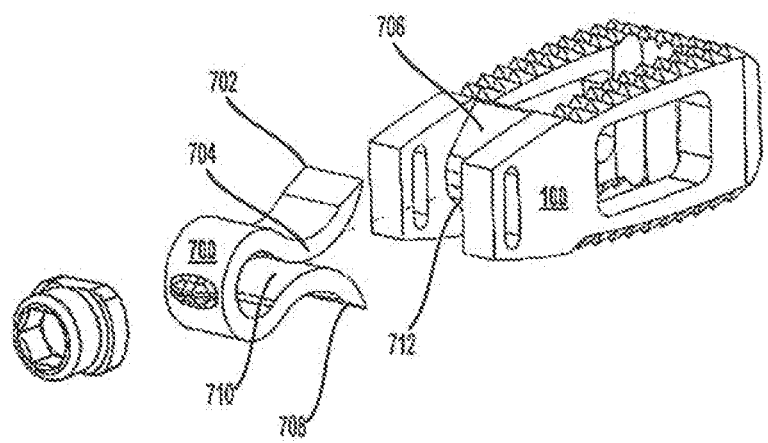
FIG. 7A-7C depict a spacer and anchor in accordance with an alternative embodiment of the present invention, wherein the upper and lower anchors of the anchoring device form a single, unitary piece.
Figure 7B:
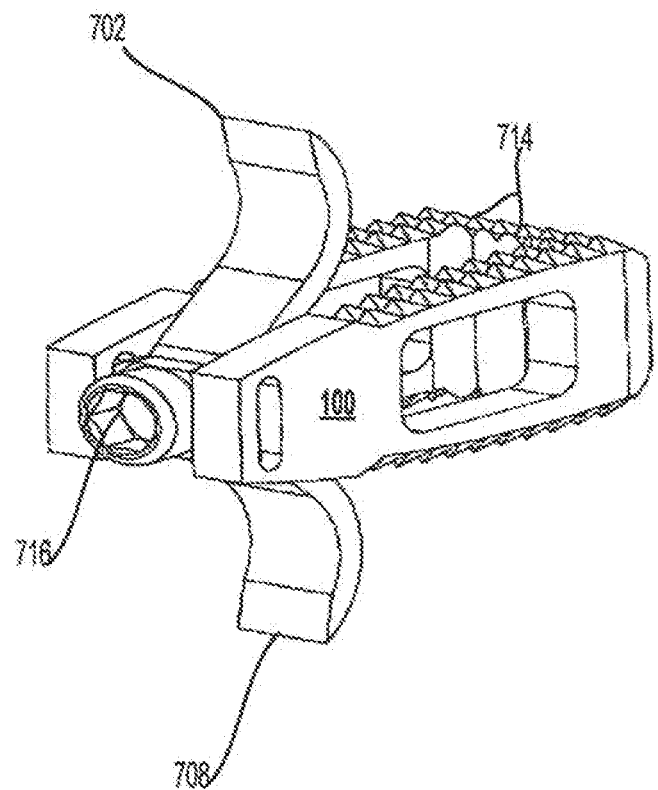
Figure 7C:
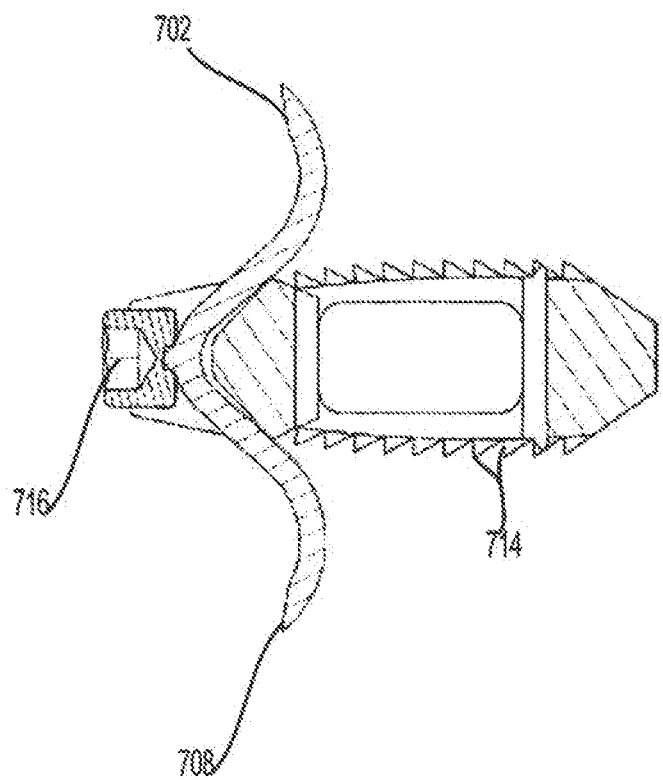

It will be clear to those skilled in the art, after reading this disclosure that numerous modification can be made to the illustrative embodiment without departing from the scope of the invention. For example, in one alternative embodiment, upper anchor 118 and lower anchor 120 can be constructed as a single unitary piece. FIGS. 7A-7C depict such an anchoring device.

As depicted in FIG. 7A, upper anchor 702 of anchoring device 700 comprises underside 704 that is adapted to press against upper inclined surface 706 of the upper guide arranged on spacer 100. Similarly, lower anchor 708 of anchoring device 700 comprises underside 710 that is adapted to press against lower inclined surface 712 of the lower guide arranged on spacer 100. As anchoring device 700 is advanced forwards, pressure causes the undersides to press against their respective inclined surfaces, which guides upper anchor 702 and lower anchor 708 to radially and simultaneously deploy into their respective vertebral bodies. As depicted in FIGS. 7B and 7C, upper anchor 702 and lower anchor 708 extend past the profile of teeth 714 to provide additional anchorage. Once the upper and lower anchors have been simultaneously deployed into their vertebra, locking cap 716 can be used to lock the anchors in their deployed position. Specifically, locking cap 716 is adapted to press the proximal end of anchoring device 700 to lock the anchoring device to spacer 100.

Figure 8A:
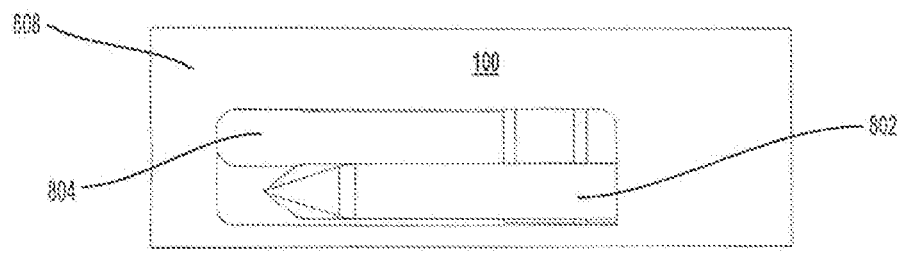
FIG. 8A-8C depict a spacer and anchor in accordance with an alternative embodiment of the present invention, wherein the upper and lower anchors of the anchoring device are disposed entirely within the spacer.
Figure 8B:
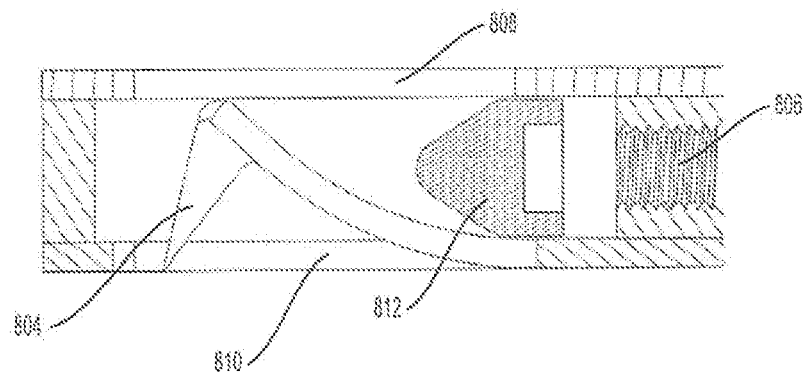
Figure 8C:
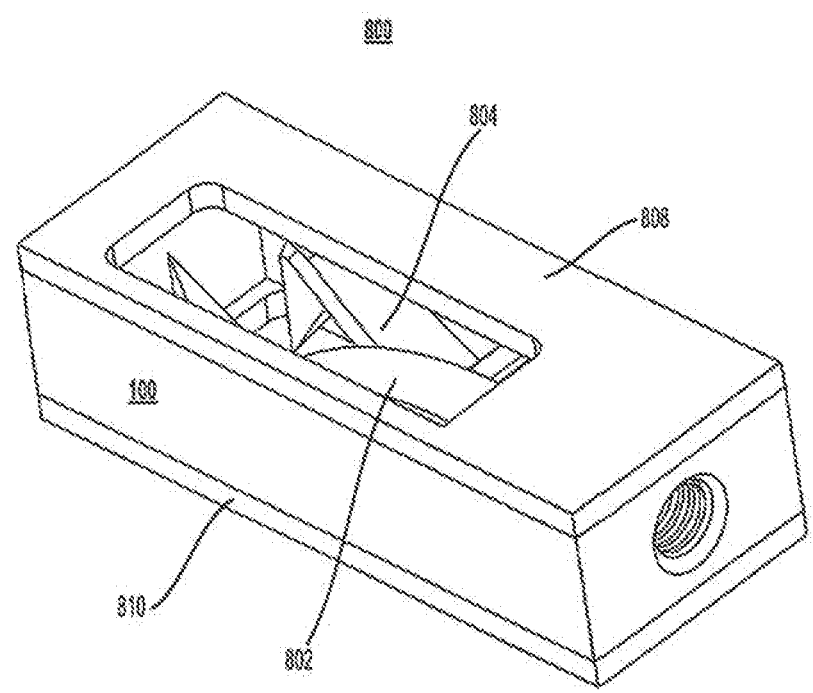

In another embodiment, as depicted in FIGS. 8A-8C, spacer 100 houses both upper anchor 802 and lower anchor 804. In other words, both the upper and lower anchors are disposed entirely within spacer 100 when the anchors are in a relaxed state. As shown in FIG. 8B, an internal drive screw 806 (i.e., an anchor drive) can be turned so that wedge 812 can be advanced forwards towards the bowed portion of both upper anchor 802 and lower anchor 804. Wedge 812 is forcibly advanced towards the bowed portion to simultaneously force upper anchor 802 and lower anchor 804 to extend through an opening arranged on superior surface 808 and inferior surface 810 of spacer 100. More precisely, as drive screw 806 is turned, wedge 812 abuts against the bowed portion of upper anchor 802 and lower anchor 804. As wedge 812 abuts against the bowed portion of the anchors, the inclined surface of wedge 810 slides along the surface of upper anchor 802 and lower anchor 804. The sliding motion applies pressure to the surfaces of the anchors, thereby forcing both upper anchor 802 and lower anchor 804 to radially extend outside of the openings of spacer 100 and into their respective intervertebral bodies.

In a further embodiment, as depicted in FIGS. 9A-9H, the anchoring device has a drive plate 906 from which upper anchor 902 and lower anchor 904 extend.

Figure 9A:
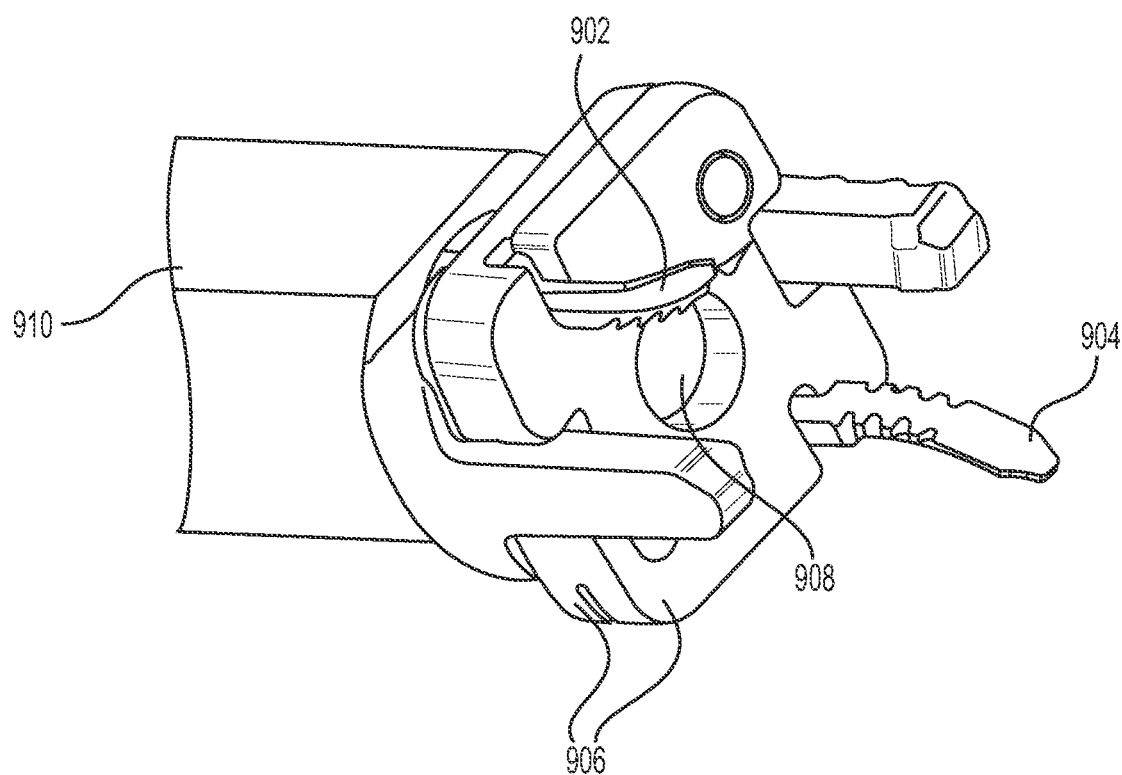
FIG. 9A-9H depict an upper anchor and a lower anchor arranged on a drive plate in accordance with an alternative embodiment of the present invention.

The drive plate of FIG. 9A includes through-hole 908 arranged at its central axis. The drive plate can be divided into four quadrants, with through-hole 908 being the origin point, like in a two-dimensional Cartesian plane. Upper anchor 902 extends from a first one of the quadrants (e.g., Quadrant I in a two-dimensional Cartesian plane), while lower anchor 904 extends from a second one of the quadrants (e.g., Quadrant III in the two-dimensional Cartesian plane), wherein the first and second quadrants are diagonally located from each other on drive plate 906. Although the anchors have been described as having a specific arrangement on drive plate 906, it will be clear to those skilled in the art after reading this disclosure that upper anchor 902 and lower anchor 904 can be arranged anywhere on the drive plate without departing from the scope of the present invention.

As further depicted in FIG. 9A, each of upper anchor 902 and lower anchor 906 has a pointed tip and a plurality of projections arranged on their lateral surfaces. The plurality of projections can be, for example, and without limitation, barbs that are angled away from the point in which the anchors penetrate into their respective vertebras. The barbs are advantageous because they make it difficult for the anchors to come loose, thus ensuring that the spacer is securely stabilized between the vertebras after implantation. FIG. 9A also depicts a pair of oppositely positioned grippers of holder 910 gripping onto the lateral surfaces of drive plate 906.

Figure 9B:
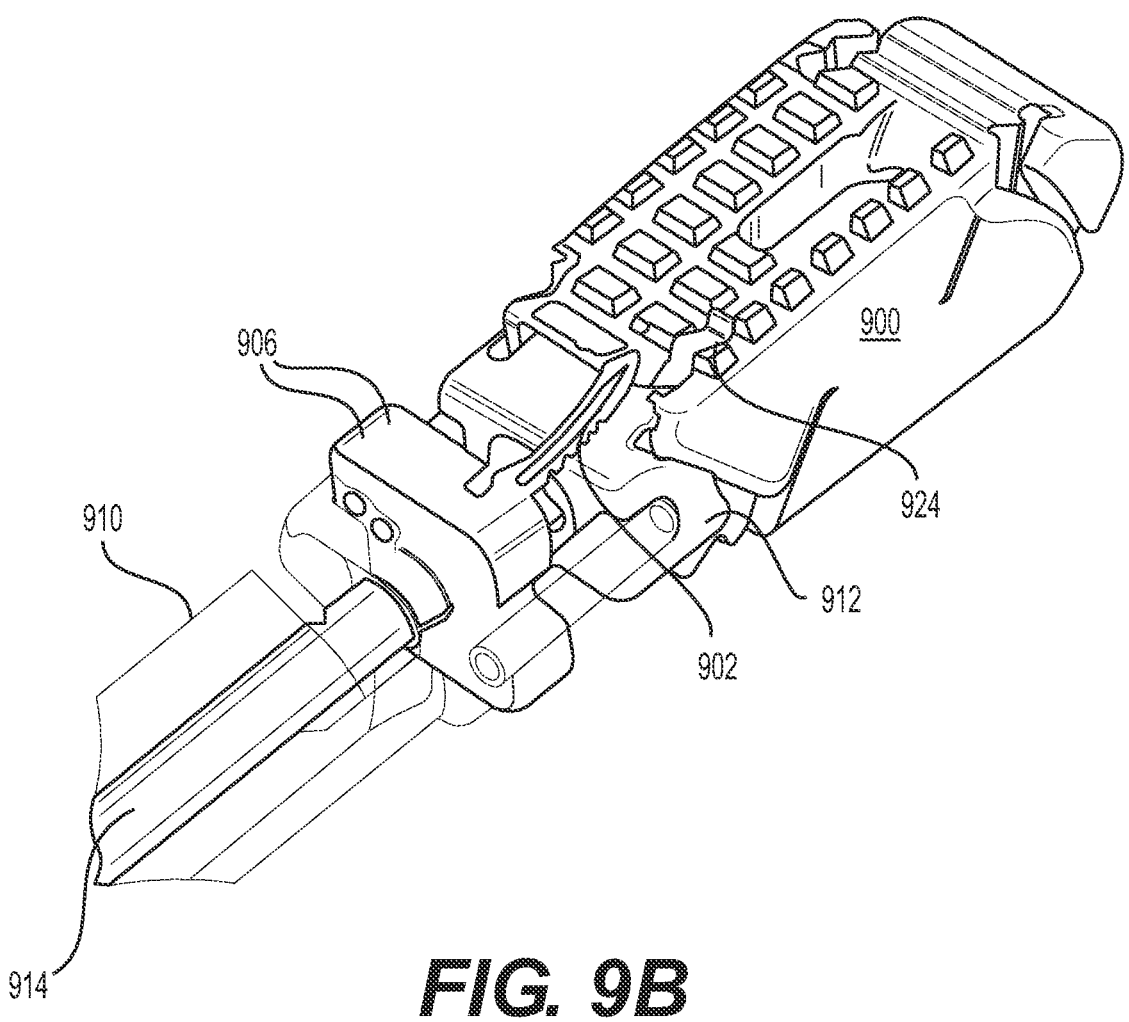
Figure 9C:
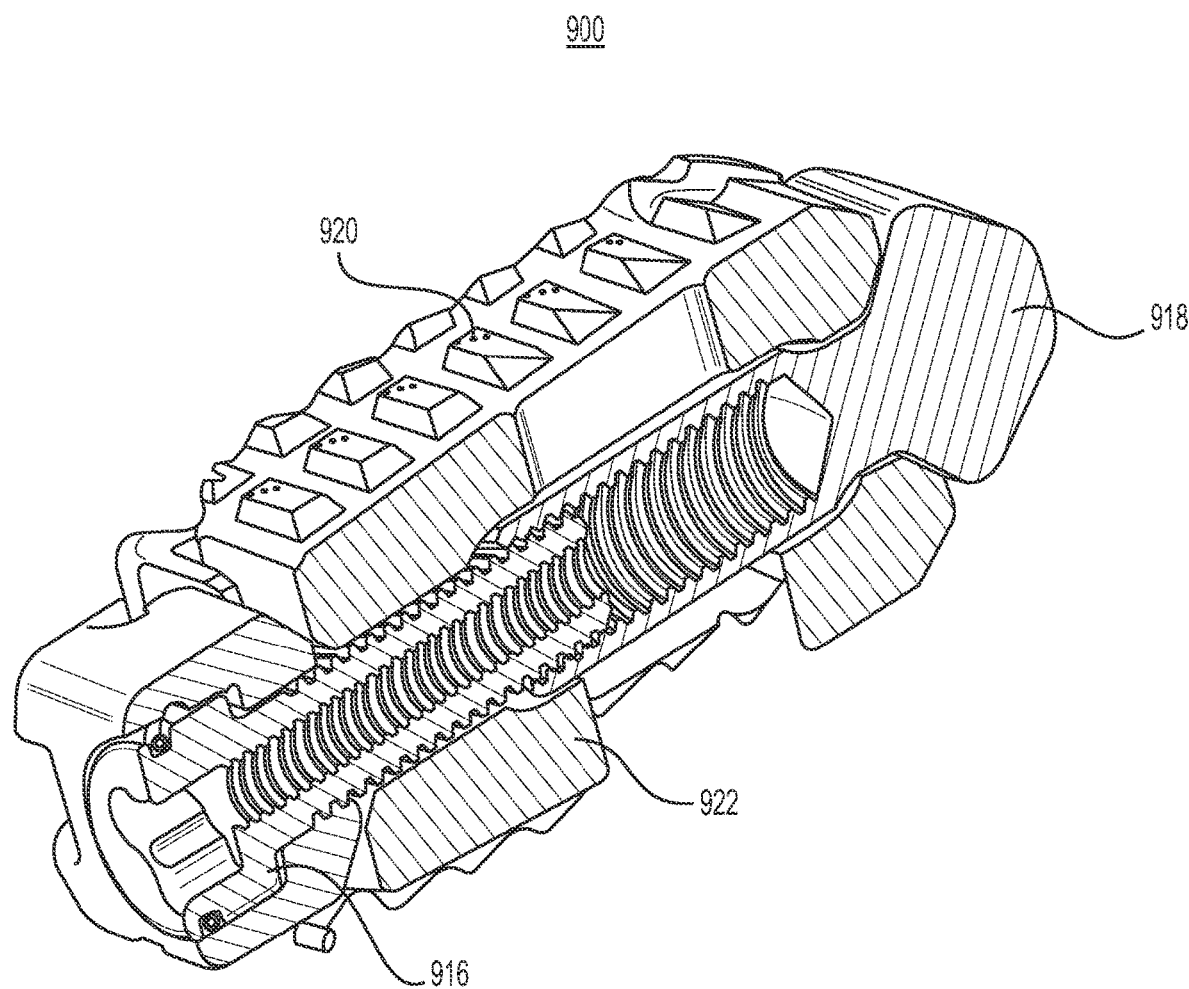
Figure 9D:
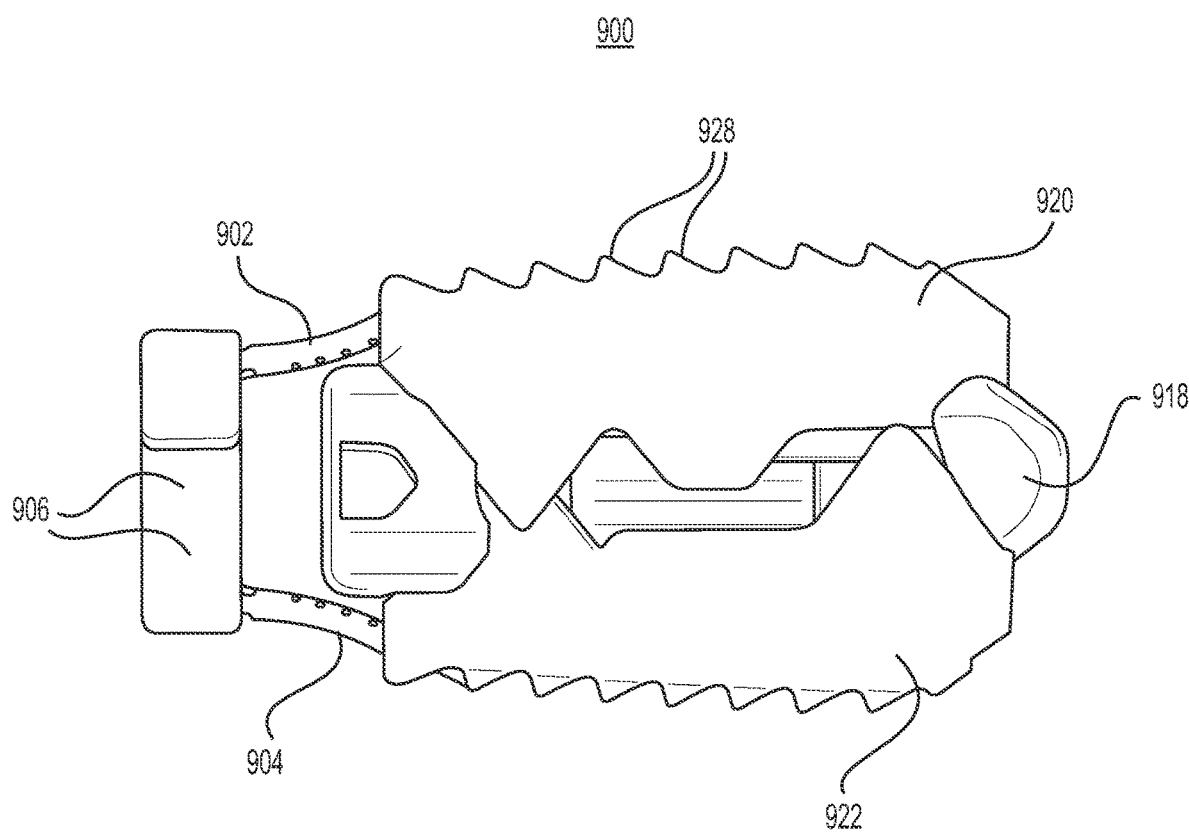

Turning now to FIG. 9B, while drive plate 906 is gripped by holder 910, a surgeon can position the grippers of holder 910 to also grip onto endplate 912 of spacer 900. Once endplate 912 is gripped by the surgeon, a driver 914 can be inserted into holder 910, which passes through through-hole 908 of drive plate 906. The driver engages one end of drive screw 916 (shown in FIG. 9C) housed within spacer 900. Once the driver has engaged the drive screw, the surgeon can turn driver 914 so that drive screw 916 can be threaded into the body of wedge 918. This causes wedge 918 to move backwards towards the proximal end of spacer 900, which in turn causes superior surface 920 and inferior surface 922 of the spacer to slide along the inclined surface of wedge 918. This can be seen more clearly in FIGS. 9C and 9D. As superior surface 920 and inferior surface 922 radially extend in opposite directions of each other, upper anchor 902 and lower anchor 904 engage upper guide 924 and lower guide 926 of spacer 900. As shown in FIG. 9D, the tips of upper anchor 902 and lower anchor 904 do not extend past the profile of teeth 928 of spacer 900, even after superior surface 920 and inferior surface 922 have been fully extended.

Figure 9E:
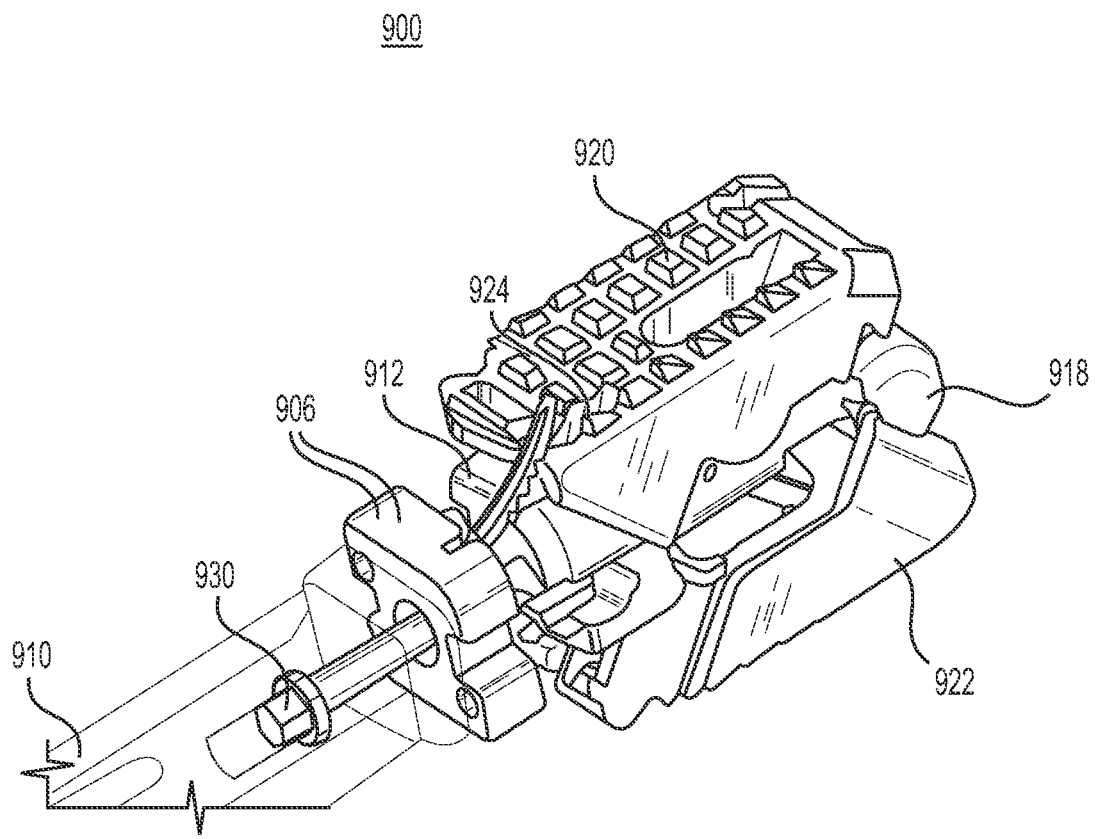
Figure 9F:
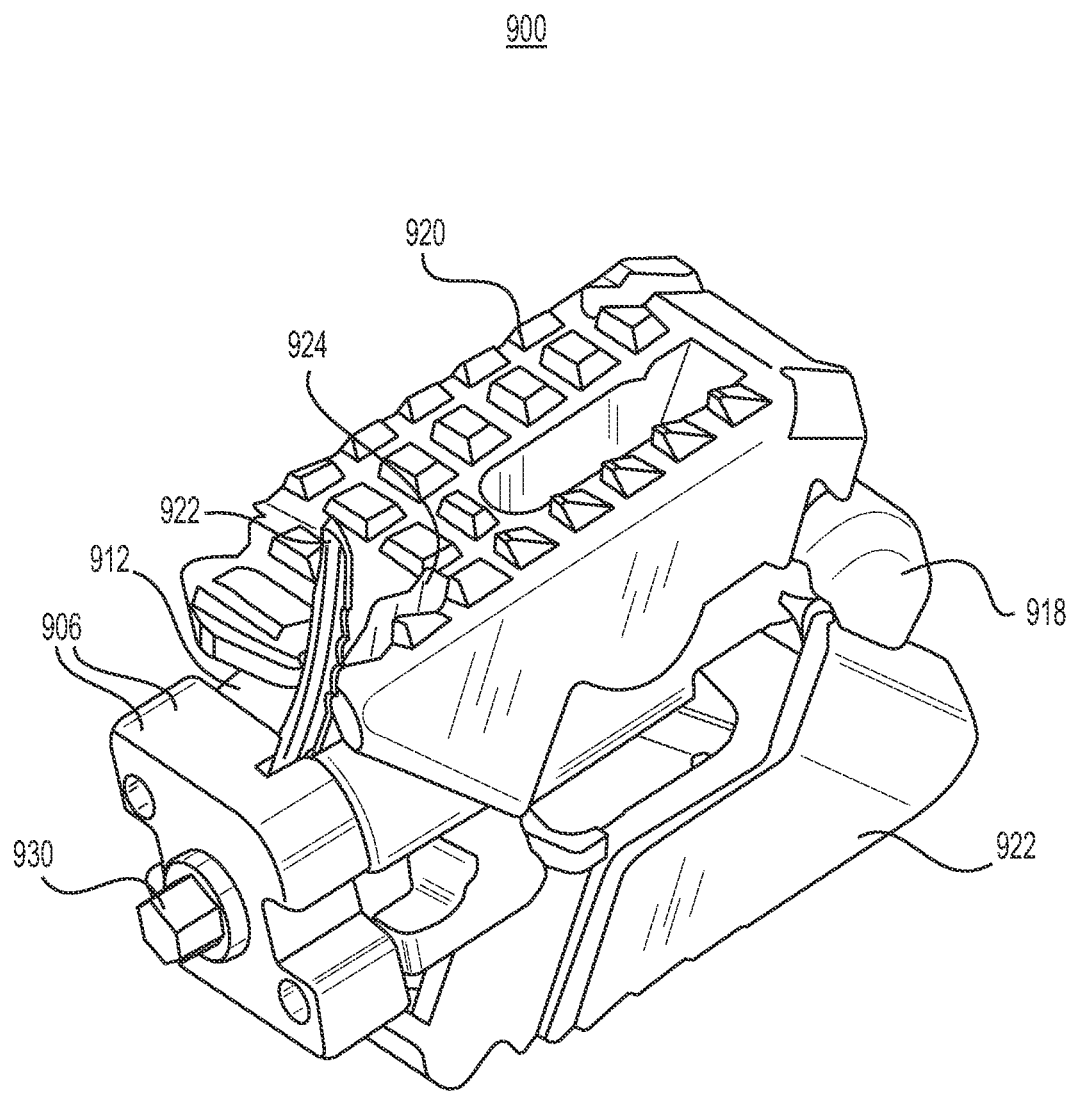
Figure 9G:
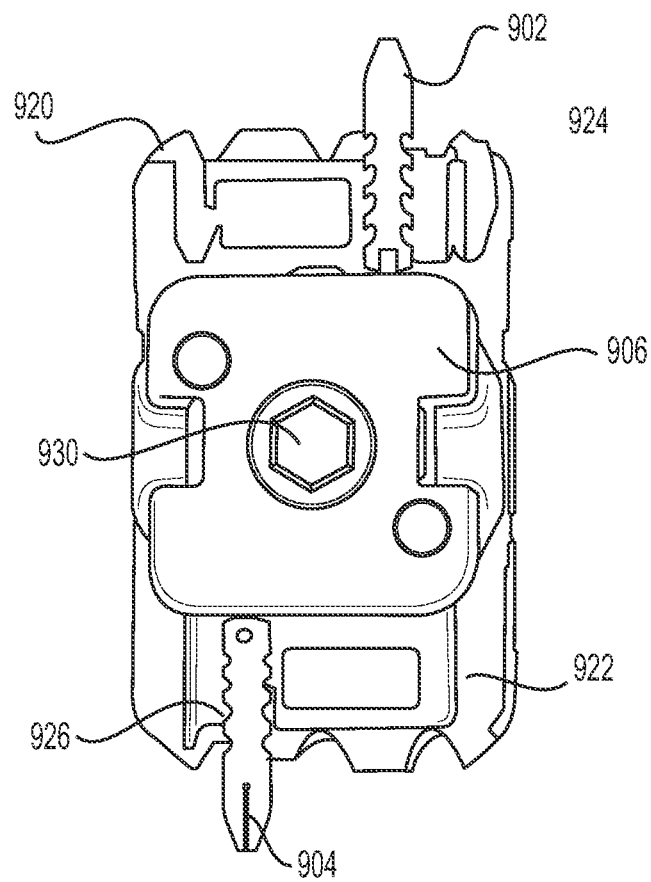
Figure 9H:
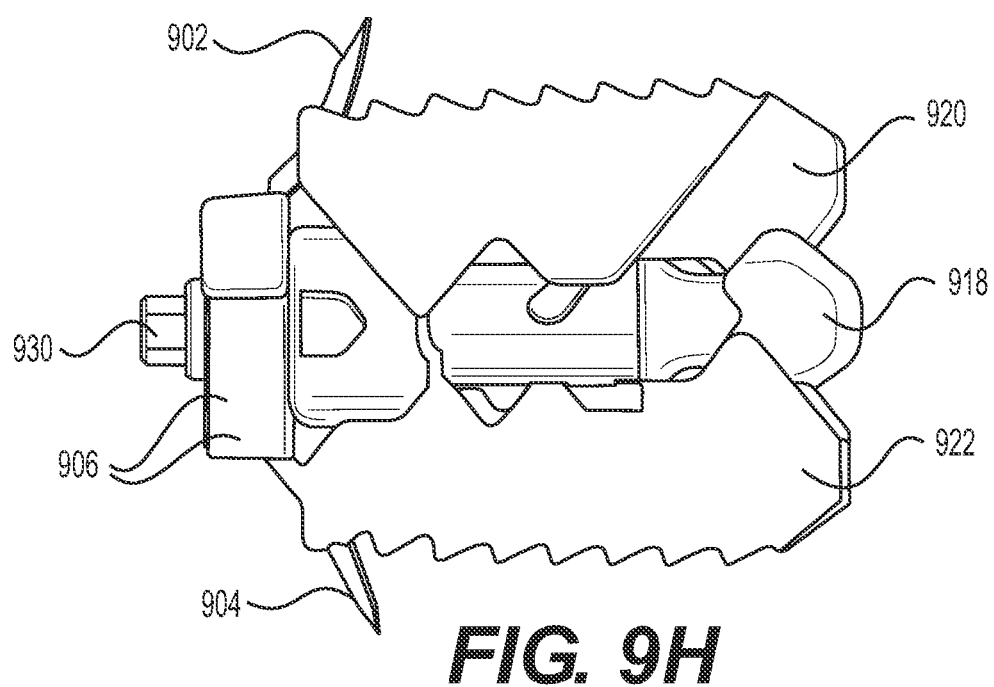

Once the superior and inferior surfaces of spacer 900 have been fully extended, the surgeon can now retract driver 914 and insert pull screw 930 (i.e., anchor driver) as shown in FIG. 9E. Pull screw 930 is physically adapted to be inserted through through-hole 908 and into the threaded hole of drive screw 916. Pull screw 930 can now be threaded to advance drive plate 906 towards the proximal end of spacer 900, which causes upper anchor 902 and lower anchor 904 to respectively slide along upper guide 924 and lower guide 926 as the drive plate is advanced towards the proximal end of the spacer. As upper anchor 902 and lower anchor 904 slide along their respective guides, the anchors simultaneously and radially extend away from spacer 900 and into their respective intervertebral bodies. Pull screw 930 is threaded by the surgeon until drive plate 906 is fully seated against endplate 912. Not only does threading pull screw 930 in this way fully deploy the anchors into their respective intervertebral bodies, it also locks the anchors to spacer 900 in a deployed position, as shown in FIGS. 9F-9H.

Figure 10:
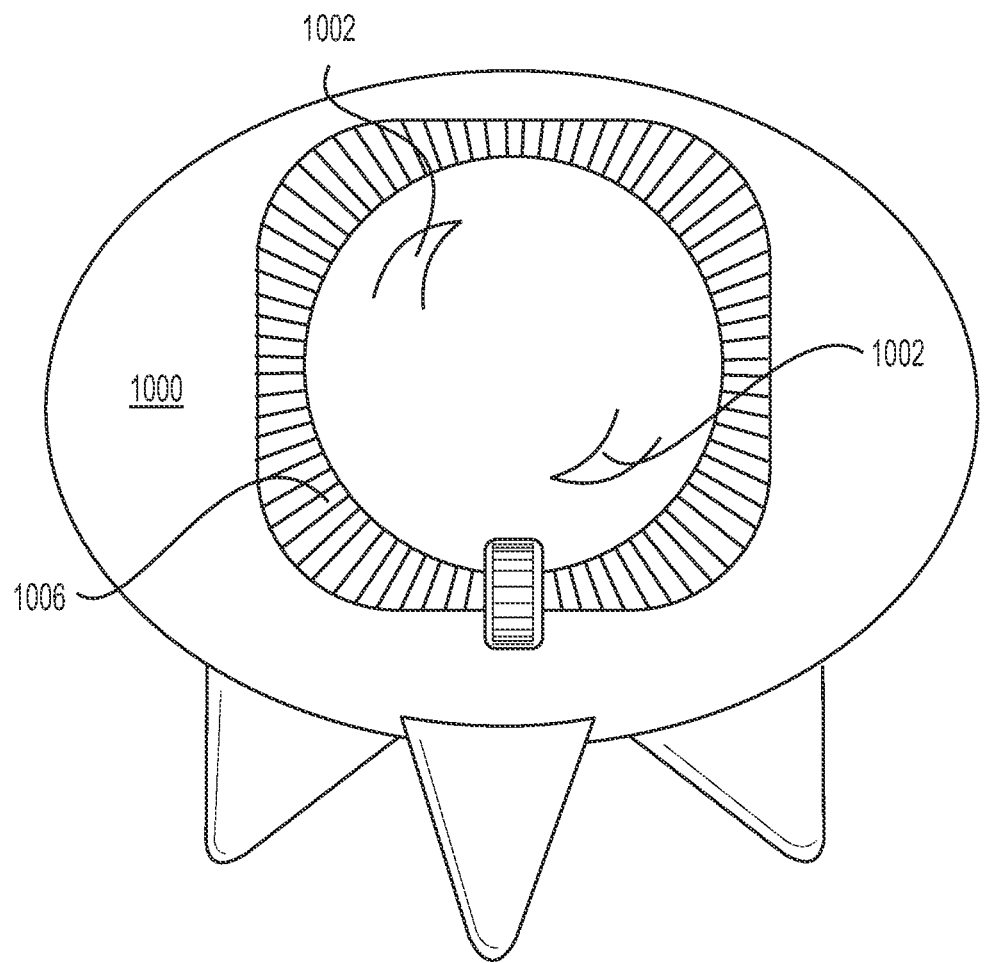
FIG. 10 depicts a spacer having worm gear for deploying one or more anchors in accordance with an alternative embodiment of the present invention.

FIG. 10 depicts a spacer-anchor combination in accordance with an alternative embodiment of the present invention. More specifically, the figure depicts spacer 1000, a plurality of upper anchors 1002, worm 1004, and gear 1006. In accordance with this embodiment, the worm is physically adapted to turn the gear, but the gear cannot turn the worm. This is because the angle on the worm is so shallow that, when the gear tries to spin it, the friction between the gear and the worm holds the worm in place. With this in mind, a surgeon can implant spacer 1000 in the disc space of adjacent vertebras. The surgeon can then use a tool to turn worm 1004 in order to rotate gear 1006 in a particular direction. As the gear rotates, upper anchors 1002 are simultaneously deployed into an intervertebral body. Once deployed, pressure from adjacent vertebras compressing down onto gear 1006 will not cause the gear to rotate. This is because, as discussed above, the angle on the worm is so shallow that the friction between the gear and the worm essentially locks the worm in place. Accordingly, upper anchors 1002 will be locked in their deployed position until worm 1004 is operated.

It is to be understood that the disclosure describes a few embodiments and that many variations of the invention can easily be devised by those skilled in the art after reading this disclosure and that the scope of the present invention is to be determined by the following claims.

What is claimed is:

1. An intervertebral fusion system comprising:
   a spacer having a superior surface, an inferior surface, opposing lateral surfaces, an upper guide, and a lower guide, wherein the spacer is adapted to be implanted between an upper vertebral body and a lower vertebral body;
   an anchoring device having an upper anchor and a lower anchor, wherein the upper and lower anchors are adapted to be simultaneously deployed into their respective vertebral bodies along the upper and lower guides when an anchor driver applies force to the upper and lower anchors simultaneously;
   a locking cap configured to lock the upper and lower anchors in their deployed position, an implantation instrument wherein the anchoring device is advanced between a pair of leaf springs of the implantation instrument to cause a first gripper and a second gripper to respectively grip a first lateral surface and a second lateral surface of the spacer,
   wherein the anchoring device presses against the upper and lower guides in order to radially deploy the upper and lower anchors into their respective vertebral bodies.

2. The intervertebral fusion system of claim 1, wherein each of the upper and lower guides has a pair of oppositely positioned lateral recesses.

3. The intervertebral fusion system of claim 1, wherein the first and second grippers are respectively adapted to pivot inwardly about a first pivot point and a second pivot point as the anchor driver is advanced between the pair of leaf springs.

4. The intervertebral fusion system of claim 1, wherein the locking cap is configured to press a proximal end of the anchoring device to lock the anchoring device to the spacer.

5. The intervertebral fusion system of claim 1, wherein each of the upper and lower anchors has a pointed tip and a plurality of barbs, and the barbs are arranged on lateral surfaces of the upper and lower anchors.

6. An intervertebral fusion device comprising:
   a spacer having a superior surface, an inferior surface, opposing lateral surfaces, an upper guide, and a lower guide, wherein the spacer is adapted to be implanted between an upper vertebral body and a lower vertebral body; and
   an anchoring device having an upper anchor and a lower anchor, wherein the upper and lower anchors are adapted to be simultaneously deployed into their respective vertebral bodies along the upper and lower guides when an anchor driver applies force to the upper and lower anchors simultaneously,
   wherein the spacer is configured to expand such that the superior surface and the inferior surface can be extended in opposite directions,
   wherein the anchoring device has a drive plate from which the upper and lower anchors extend, the drive plate having a through-hole for receiving a pull screw; and the pull screw is adapted to be threaded into a threaded hole arranged within the spacer for advancing the drive plate towards the spacer.

7. The intervertebral fusion device of claim 6, wherein the upper and lower anchors respectively slide along the upper and lower guides as the drive plate is advanced towards the spacer to simultaneously and radially extend away from the spacer and into their respective intervertebral bodies.

8. The intervertebral fusion device of claim 7, wherein the drive plate includes four quadrants; the upper anchor extends from a first one of the quadrants; and the lower anchor extends from a second one of the quadrants, the first and second quadrants being diagonally located from each other.

* * * * *